United States Patent
Hara

(10) Patent No.: US 12,234,466 B2
(45) Date of Patent: Feb. 25, 2025

(54) ASPERGILLUS MICROORGANISM CARRYING DISRUPTIONS OF MULTIPLE GENES AND A METHOD OF PRODUCING THEREOF

(71) Applicant: KIKKOMAN CORPORATION, Noda (JP)

(72) Inventor: Seiichi Hara, Noda (JP)

(73) Assignee: KIKKOMAN CORPORATION, Noda (JP)

( * ) Notice: Subject to any disclaimer, the term of this patent is extended or adjusted under 35 U.S.C. 154(b) by 925 days.

(21) Appl. No.: 17/289,047

(22) PCT Filed: Nov. 4, 2019

(86) PCT No.: PCT/JP2019/043173
§ 371 (c)(1),
(2) Date: Apr. 27, 2021

(87) PCT Pub. No.: WO2020/095864
PCT Pub. Date: May 14, 2020

(65) Prior Publication Data
US 2021/0403929 A1    Dec. 30, 2021

(30) Foreign Application Priority Data

Nov. 5, 2018 (JP) ................................ 2018-208022
Jun. 12, 2019 (JP) ................................ 2019-109602

(51) Int. Cl.
*C12N 15/80* (2006.01)
*C12N 1/14* (2006.01)
*C12N 15/52* (2006.01)

(52) U.S. Cl.
CPC ............... *C12N 15/80* (2013.01); *C12N 1/14* (2013.01); *C12N 15/52* (2013.01); *C12N 2800/102* (2013.01)

(58) Field of Classification Search
None
See application file for complete search history.

(56) References Cited

U.S. PATENT DOCUMENTS

| 2006/0183233 A1 | 8/2006 | Kempe |
| 2019/0035999 A1 | 1/2019 | Najafi |
| 2019/0359991 A1* | 11/2019 | Tsuboi ................ C12N 15/102 |

FOREIGN PATENT DOCUMENTS

| JP | 2006158269 | 6/2006 |
| WO | 2017135317 | 8/2017 |

OTHER PUBLICATIONS

Tani, S. et al. "Reversible impairment of the ku80 gene by a recyclable marker in Aspergillus aculeatus" AMB Express, 2013, 3:4, https://amb-express.springeropen.com/articles/10.1186/2191-0855-3-4.

Goosen, T. et al "Tryptophan auxotrophic mutants in Aspergillus niger: Inactivation of the trpC gene by cotransformation mutagenesis" Molecular and General Genetics, 1989, vol. 219, p. 282-288.

Toyn, J. H. et al. "A counterselection for the tryptophan pathway in yeast: 5-fluoroanthranilic acid resistance" Yeast, 2000, vol. 16, p. 553-560.

Nielsen, M. L. et al. "Efficient PCR-based gene targeting with a recyclable marker for Aspergillus nidulans" Fungal Genetics and Biology, 2006, vol. 43, No. 1, p. 54-64.

Takahashi, T. et al. "Enhanced gene targeting frequency in ku70 and ku80 disruption mutants of Aspergillus sojae and Aspergillus oryzae" Molecular Genetics and Genomics, 2006, vol. 275, No. 5, p. 460-470.

Office Action from JPO (Japanese version and English Machine Translation)Japanese Patent Application No. 2019-109602, Jul. 1, 2019.

International Search Report of PCT/JP2019/043173.

Extended European Search Report of corresponding EP patent Application No. 19882317.1 Date of Drafting: Sep. 30, 2022.

Nguyen Havy N et al "Targeted cloning of a large gene cluster from Lecanicillium genome by Cre/loxP based method" J Microbiol Methods. Jul. 2018;150:47-54. doi: 10.1016/j.mimet.2018.05.017. Epub May 23, 2018.

T. Takahashi et al "generations of large chromosomal deletions in koji molds aspergillus oryzae and aspergillus sojae via a loop-out recombination" Appl Environ Microbiol. Dec. 2008;74(24):7684-93. doi: 10.1128/AEM.00692-08. Epub Oct. 24, 2008.

J'S Horng et al"Cloning and characterization of the trpC gene from an aflatoxigenic strain of Aspergillus parasiticus", Appl Environ Microbiol. Oct. 1989;55(10):2561-8. doi: 10.1128/aem.55.10.2561-2568.1989.

Takahashi T et al "Efficient gene disruption in the koji-mold Aspergillus sojae using a novel variation of the positive-negative method", Mol Genet Genomics. Oct. 2004;272(3):344-52. doi: 10.1007/s00438-004-1062-0. Epub Sep. 16, 2004.

Office action from Chinese Patent Office (English machine translation) from Patent Application No. 201980071269.X Date of Drafting: Aug. 12, 2023.

Tadashi Takahashi et al., Appl Environ Microbiol, vol. 74, No. 24, pp. 7684-7693, 2008.

J S Horng et al. Appl Environ Microbiol vol. 55, No. 10, pp. 2561-2568, 1989.

Notification of transmittal of translation of the international preliminary report on patentability (Form PCT/IB/338) for International Patent Application No. PCT/JP2019/043173.

(Continued)

*Primary Examiner* — Allison M Fox
*Assistant Examiner* — Qinhua Gu
(74) *Attorney, Agent, or Firm* — JMB Davis Ben-David

(57) ABSTRACT

The objective of the present invention is to provide a transformed *Aspergillus* microorganism lacking at least two types of selection marker genes available for marker recycling method and a composition therefor. The objective can be achieved by a transformed *Aspergillus* microorganism lacking at least two types of selection marker genes available for marker recycling method on its chromosomes, or a composition for transforming an *Aspergillus* microorganism containing at least two types of nucleic acid fragments containing a loop-out region and a selection marker gene available for marker recycling method between homologous recombination regions, wherein the selection marker genes contain a tryptophan biosynthesis gene and a gene different from tryptophan biosynthesis gene.

9 Claims, 18 Drawing Sheets
Specification includes a Sequence Listing.

(56) References Cited

OTHER PUBLICATIONS

Translation of International preliminary report on patentability (Form PCT/IPEA409) for International Patent Application No. PCT/JP2019/043173.
Chinese Office action (English machine translation of Office Action) Corresponding Patent Application No. 201980071269.X Date of Drafting: May 10, 2024.

* cited by examiner

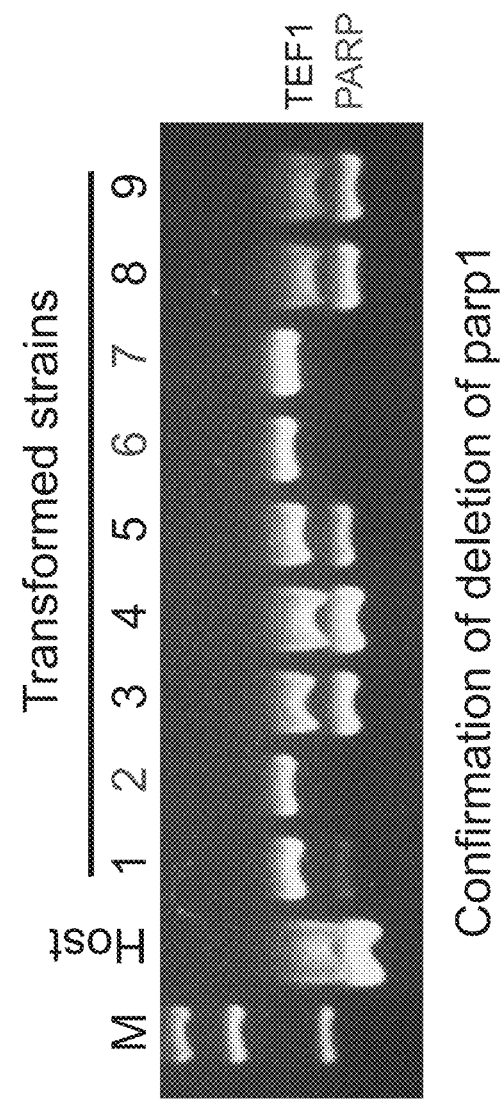

Confirmation of homologous recombination

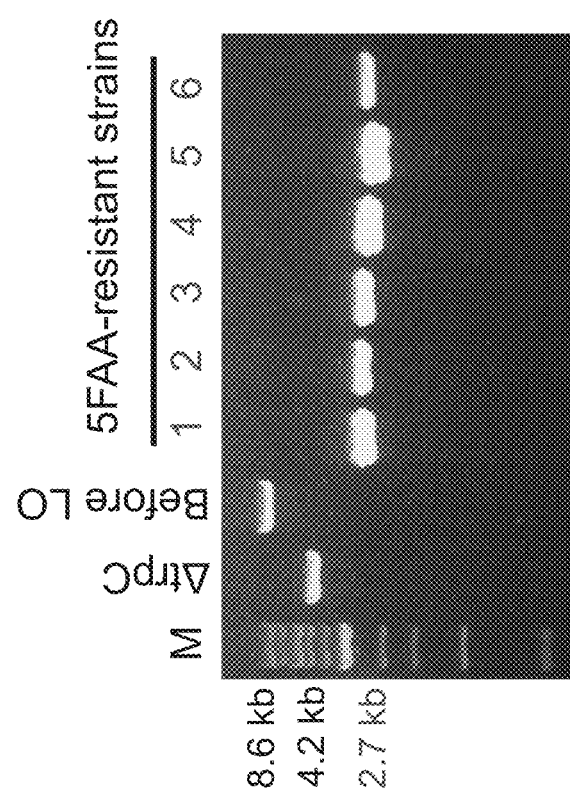

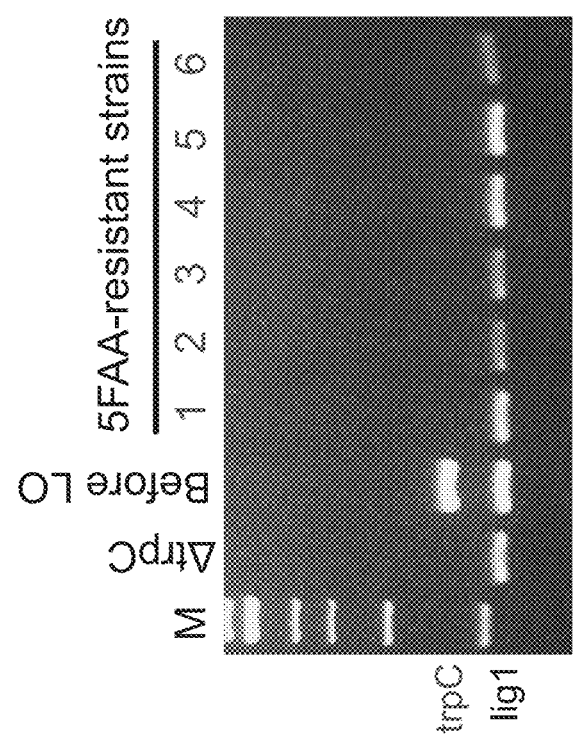

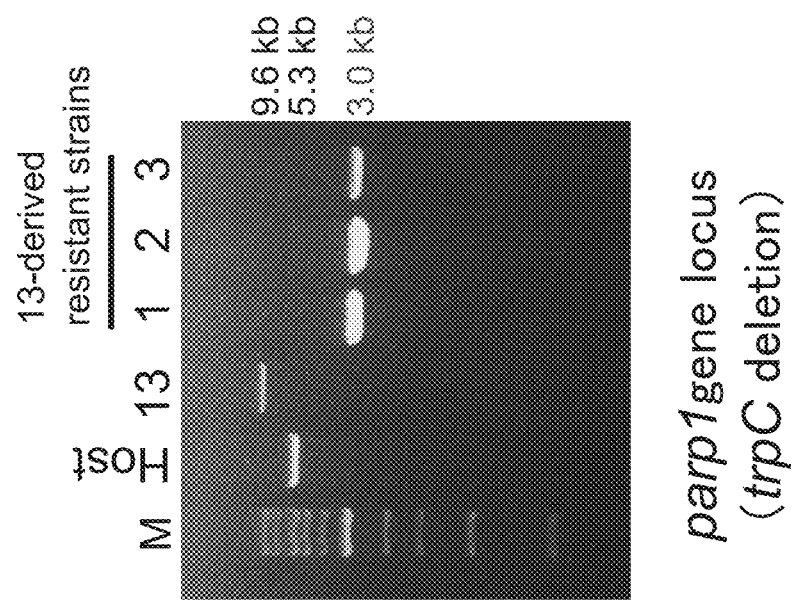

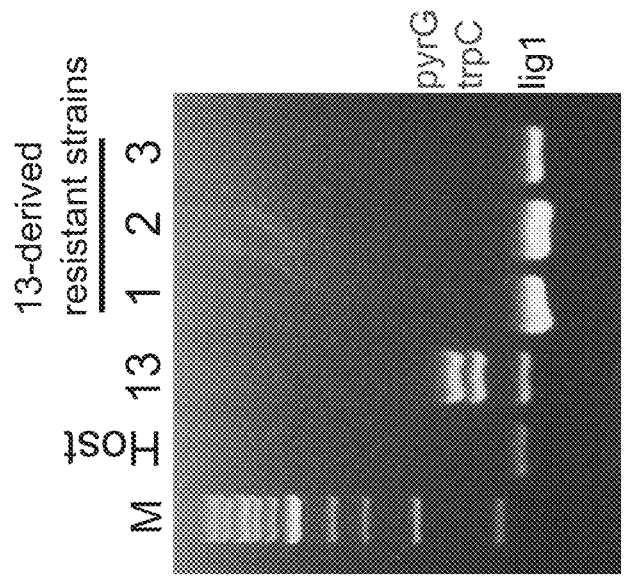

ASPERGILLUS MICROORGANISM CARRYING DISRUPTIONS OF MULTIPLE GENES AND A METHOD OF PRODUCING THEREOF

This is the US National Stage of International Patent Application No. PCT/JP2019/043173 filed on Nov. 4, 2019, which in turn claims priority to Japanese Patent Application No. 2018-208022 filed on Nov. 5, 2018 and Japanese Patent Application No. 2019-109602 filed on Jun. 12, 2019, which are incorporated herein by reference in their entirety.

TECHNICAL FIELD

The present invention relates to a transformed *Aspergillus* microorganism having disruption of at least two types of genes on its chromosomes and a method of producing the same.

BACKGROUND ART

*Aspergillus* microorganisms are used in the manufacturing process of koji, which is one of the processes of producing fermented foods such as soy sauce and miso, and are also used in the production of various other substances. Therefore, there is a demand for technology to modify *Aspergillus* microorganisms so as to express desired phenotypes, for example, by disrupting target genes on its chromosomes.

Among methods for disrupting a target gene on chromosomes of a host organism is marker recycle method (also called marker recycling method). Marker recycling method includes the steps of replacing a target gene with a selection marker gene by homologous recombination, and then removing the selection marker gene so that the selection marker gene does not remain on chromosomes of the transformant and the selection marker gene can be reused.

As for the selection marker genes used in marker recycling method, it is preferable to be able to easily confirm the replacement by the selection marker gene and the removal of the selection marker gene. The pyrG gene is used in *Aspergillus* microorganisms as a selection marker gene available for marker recycling method.

*Aspergillus* microorganisms carrying the pyrG gene on its chromosomes can grow without uridine and/or uracil (hereinafter also referred to as uridine/uracil), but metabolize 5-fluoroorotic acid (5-FOA), which is an analog of orotidine 5'-monophosphate, an intermediate in the biosynthesis of uridine monophosphate, to produce the toxic substance, 5-fluorouracil (5-FU). Therefore, *Aspergillus* microorganisms carrying the pyrG gene on its chromosomes cannot grow when cultured in the presence of 5-FOA. In contrast, *Aspergillus* microorganisms without the pyrG gene on its chromosomes cannot metabolize 5-FOA, and therefore can grow in the presence of 5-FOA, but are uridine/uracil auxotroph.

Like the pyrG gene, as for the selection marker gene available for marker recycling method, it is preferable to be a selection marker gene that can be used for a counter selection system that makes use of the fact that the expression of the gene prevents an *Aspergillus* microorganism from growing in an environment containing a certain agent (such as 5-FOA). In other words, if no agent used for the counter selection system has been found, the selection marker gene cannot be used in the marker recycling method.

Using this system, by selecting a transformant replacing a target gene on chromosomes of the pyrG-gene-deficient *Aspergillus* microorganism with the pyrG gene with the use of uridine/uracil-free medium followed by counter-selecting the selected transformant with the use of 5-FOA-containing medium, the transformant lacking the target gene and the pyrG gene can be obtained as a 5-FOA resistant strain.

However, at present, the pyrG gene is the only selection marker gene used in marker recycling method for *Aspergillus* microorganisms. In the counter selection systems using a niaD-deficient strain and a sC-deficient strain with the respective drugs, both of them are rarely used in marker recycling method because the background growth of non-deficient strains is observed due to the weak selection pressure of the drugs.

On the other hand, Patent Document 1 (the entire description is incorporated by reference herein) describes that the presence or absence of a defect in the trpC gene, which is a gene involved in the biosynthesis of tryptophan, is evaluated by confirming the growth of a transformant of *Rhizopus delemar* in the presence of 5-fluoroanthranilic acid (5-FAA). Non-Patent Document 1 (the entire description is incorporated by reference herein) describes a transformed *Aspergillus aculeatus* lacking as selection marker genes the pyrG gene, and the argB gene that is an arginine biosynthesis gene. Non-Patent Document 2 (the entire description is incorporated by reference herein) describes the irreversible deletion of the trpC gene in *Aspergillus niger*. Non-Patent Document 3 (the entire description is incorporated by reference herein) describes applying the TRP1 marker gene of yeast (*Saccharomyces cerevisiae*) that is completely different from *Aspergillus* microorganisms to the counter selection system.

CITATION LIST

Patent Literature

Patent Document 1, WO 2017/135317

Non-Patent Literature

Non-Patent Document 1: TANI et al., AMB Express, 2013, 3:4, https://amb-express.springeropen.com/articles/10.1186/2191-0855-3-4

Non-Patent Document 2: GOOSEN et al, Molecular and General Genetics, 1989, Vol. 219, P. 282-288

Non-Patent Document 3: TOYN et al, Yeast, 2000, Vol. 16, P. 553-560

SUMMARY OF THE INVENTION

Problems to be Solved by the Invention

In Patent Document 1, a trpC gene-deficient strain is selected based on whether or not it grows in the presence of 5-FAA. However, Patent Document 1 fails to disclose the use of the trpC gene as a recyclable selection marker gene used in marker recycling method.

In addition, as for the transformed *Aspergillus aculeatus* disclosed in Non-Patent Document 1, the missing argB gene is not a selectaion marker gene that can be used in marker recycling method. Non-Patent Document 1 falis to disclose the use of another selection marker gene in place of the argB gene, for example, the use of a certain selection marker gene extracted from among a large number of genes involved in amino acid biosynthesis.

Furthermore, little is known so far about any selection marker gene that can be recycled to the same extent as the pyrG gene, and can be used in place of the pyrG gene when transforming a host organism, *Aspergillus* microorganism, in marker recycling method. In particular, little is also known about any system that can easily confirm the replacement and removal by the selection marker gene which is available for marker recycling method directed to *Aspergillus* microorganisms and which can be used together with the pyrG gene. There is no disclosure of the above selection marker gene and system even in Non-Patent Documents 2 and 3. In particular, the present inventors have found that *Aspergillus* microorganisms have no gene corresponding to the yeast's TRP1 marker gene.

In view of the above circumstances, it is a first objective of the present invention to provide a transformed *Aspergillus* microorganism lacking at least two types of selection marker genes available for marker recycling method and a method of producing the transformant.

It is a second objective of the present invention to provide a method for lacking at least two types of target genes on chromosomes of a transformed *Aspergillus* microorganism applying marker recycling method with the use of a composition containing at least two types of nucleic acid fragments containing a selection marker gene.

Means for Solving the Problems

In the course of extensive efforts to find a way to solve the above-identified problems, the present inventors came to focus on genes involved in the biosynthesis of tryptophan among the various genes that were possibly used. Then, the present inventors introduced a nucleic acid fragment containing a loop-out region and a tryptophan biosynthesis gene into the locus of the target gene using the transformed *Aspergillus* microorganism lacking the tryptophan biosynthesis gene as a host organism. As a result, the present inventors confirmed the replacement of the target gene with the tryptophan biosynthesis gene by growth in the absence of tryptophan. Furthermore, the present inventors found that the removal of the tryptophan biosynthesis gene by looping out could be accomplished by the growth in the presence of 5-FAA.

Surprisingly, the present inventors succeeded in producing and selecting a double-disrupted transformed *Aspergillus* microorganism lacking the pyrG gene and the tryptophan biosynthesis gene as selection marker genes by controlling the amounts of 5-FOA and 5-FAA at predetermined concentrations. The genus *Aspergillus* such as *Aspergillus* soya and *Aspergillus oryzae* are known to be highly resistant to drugs. For this reason, there has been no knowledge on whether or not 5-FAA can be used for counter-selecting a tryptophan-biosynthesis-gene-deficient strain of *Aspergillus* microorganism, and if so, what concentration of 5-FAA should be used. In addition to this, the weak selective pressure, i.e., the small difference between sensitivity and resistance, may even make it difficult to determine a suitable drug concentration. Despite this technical background, the present inventors succeeded in producing and selecting the above-mentioned double-disrupted transformed *Aspergillus* microorganism, and also in the efficient and rapid deletion of two types of target nucleic acids on its chromosomes by using the double-disrupted transformed *Aspergillus* microorganism. The present invention has been completed based on these findings and successful examples.

Thus, according to each aspect of the present invention, the following are provided.

[1] A transformed *Aspergillus* microorganism lacking at least two types of selection marker genes available for marker recycling method on its chromosomes, wherein the selection marker genes contain a tryptophan biosynthesis gene and a gene different from tryptophan biosynthesis gene.

[2] A composition for transforming a *Aspergillus* microorganism containing at least two types of nucleic acid fragments containing a loop-out region and a selection marker gene available for marker recycling method between homologous recombination regions, wherein the nucleic acid fragments contain a nucleic acid fragment in which the selection marker gene is a tryptophan biosynthesis gene and a nucleic acid fragment in which the selection marker gene is a gene different from tryptophan biosynthesis gene.

[3] The transformed *Aspergillus* microorganism or composition according to any one of [1] to [2] above, wherein the host organism of the transformed *Aspergillus* microorganism is a microorganism of the genus *Aspergillus* different from *Aspergillus aculeatus*.

[4] The transformed *Aspergillus* microorganism or composition according to any one of [1] to [3] above, wherein the gene different from tryptophan biosynthesis gene is a gene that complements a requirement for a nutritional substance and is involved in biosynthesizing a toxic substance from an analogue of the nutritional substance.

[5] The transformed *Aspergillus* microorganism or composition according to any one of [1] to [4] above, wherein the gene different from tryptophan biosynthesis gene is a selection marker gene selected from the group consisting of uracil biosynthesis genes, sulfate metabolism genes, and nitrate metabolism genes.

[6] The transformed *Aspergillus* microorganism or composition according to any one of [1] to [5] above, wherein the tryptophan biosynthesis gene is trpC gene and the gene different from tryptophan biosynthesis gene is at least one gene selected from the group consisting of pyrG gene, niaD gene, and sC gene.

[7] A method of producing a transformed *Aspergillus* microorganism lacking first and second selection marker genes available for marker recycling method on its chromosomes, wherein among the first and second selection marker genes, one is a tryptophan biosynthesis gene and the other is a gene that complements a requirement for a nutritional substance and is involved in biosynthesizing a toxic substance from an analogue of the nutritional substance, and the method includes the steps of:

(1) subjecting a transformed *Aspergillus* microorganism lacking the first selection marker gene on its chromosomes to homologous recombination targeting the second selection marker gene on its chromosomes with the use of a nucleic acid fragment containing a loop-out region and the first selection marker gene between homologous recombination regions, thereby obtaining a transformed *Aspergillus* microorganism;

(2) culturing the transformed *Aspergillus* microorganism obtained in the step (1) in the presence of a nutritional substance corresponding to the second selection marker gene to select a transformed *Aspergillus* microorganism inserting the first selection marker gene on its chromosomes and lacking the second selection marker gene on its chromosomes; and (3) culturing the transformed *Aspergillus* microorganism selected in the step (2) in the presence of a nutritional substance corresponding to the first selection marker gene and an analogue of the nutritional substance as well as a nutritional substance corresponding to the second selection marker gene to select a transformed *Aspergillus* microorganism lacking the first and second selection marker genes on its chromosomes.

[8] A method for lacking two types of target genes on chromosomes of a transformed *Aspergillus* microorganism with the use of first and second selection marker genes available for marker recycling method, wherein among the first and second selection marker genes, one is a tryptophan biosynthesis gene and the other is a gene that complements a requirement for a nutritional substance and is involved in biosynthesizing a toxic substance from an analogue of the nutritional substance, and the method includes the steps of:

(A) subjecting a transformed *Aspergillus* microorganism lacking the first and second selection marker genes on its chromosomes to homologous recombination targeting the first and second target genes on its chromosomes with the use of a first nucleic acid fragment containing a loop-out region and the first selection marker gene between homologous recombination regions for the first target gene and a second nucleic acid fragment containing a loop-out region and the second selection marker gene between homologous recombination regions for the second target gene, thereby obtaining a transformed *Aspergillus* microorganism; and (B) culturing the transformed *Aspergillus* microorganism obtained in the step (A) in the absence of nutritional substances corresponding to the first and second selection marker genes to select a transformed *Aspergillus* microorganism inserting the first and second selection marker genes on its chromosomes.

[9] The method according to [8] above, further containing the step of:

(C) culturing the transformed *Aspergillus* microorganism selected in the step (B) in the presence of a nutritional substance corresponding to the first selection marker gene and an analogue of the nutritional substance as well as a nutritional substance corresponding to the second selection marker gene and an analogue of the nutritional substance to select a transformed *Aspergillus* microorganism lacking the first and second selection marker genes and the first and second target genes on its chromosomes.

[10] The method according to [9] above, wherein the first selection marker gene is a tryptophan biosynthesis gene, and the analogue of the nutritional substance corresponding to the first selection marker gene is 5-FAA, and the concentration of 5-FAA is in the range between 0.005% (w/v) and 0.02% (w/v); and the second selection marker gene is pyrG gene, and the analogue of the nutritional substance corresponding to the second selection marker gene is 5-FOA, and the concentration of 5-FOA is in the range between 0.05% (w/v) and 0.15% (w/v).

[11] The method according to any one of [7] to [10] above, wherein the host organism of the transformed *Aspergillus* microorganism is a microorganism of the genus *Aspergillus* different from *Aspergillus aculeatus*.

[101] A transformed *Aspergillus* microorganism lacking at least two types of genes, wherein the genes are selection marker genes available for marker recycling method on its chromosomes, and the selection marker genes contains trpC gene and pyrG gene.

[102] A composition for transforming an *Aspergillus* microorganism, comprising at least two types of nucleic acid fragments containing a loop-out region and a selection marker gene available for marker recycling method between homologous recombination regions, wherein the nucleic acid fragments contain a nucleic acid fragment in which the selection marker gene is trpC gene and a nucleic acid fragment in which the selection marker gene is pyrG gene.

[103] The method according to any one of [101] to [102] above, wherein the host organism of the transformed *Aspergillus* microorganism is a microorganism of the genus *Aspergillus* different from *Aspergillus aculeatus*, preferably selected from the group consisting of *Aspergillus sojae*, *Aspergillus oryzae*, *Aspergillus tamarii*, *Aspergillus luchuensis*, *Aspergillus usamii* and *Aspergillus saitoi*.

[104] A method of producing a transformed *Aspergillus* microorganism, wherein the transformed *Aspergillus* microorganism lacks first and second selection marker genes available for marker recycling method on its chromosomes; among the first and second selection marker genes, one is trpC gene and the other is pyrG gene; the nutritional substance corresponding to the trpC gene is tryptophan and the analogue of tryptophan is 5-FAA; the nutritional substance corresponding to the pyrG gene is uridine and/or uracil and the analogue of uridine and/or uracil is 5-FOA; and the method includes the steps of:

(1) subjecting a transformed *Aspergillus* microorganism lacking the first selection marker gene on its chromosomes to homologous recombination targeting the second selection marker gene on its chromosomes with the use of a nucleic acid fragment containing a loop-out region and the first selection marker gene between homologous recombination regions, thereby obtaining a transformed *Aspergillus* microorganism;

(2) culturing the transformed *Aspergillus* microorganism obtained in the step (1) in the presence of the nutritional substance corresponding to the second selection marker gene to select a transformed *Aspergillus* microorganism inserting the first selection marker gene on its chromosomes and lacking the second selection marker gene on its chromosomes; and (3) culturing the transformed *Aspergillus* microorganism selected in the step (2) in the presence of a nutritional substance corresponding to the first selection marker gene and an analogue of the nutritional substance as well as a nutritional substance corresponding to the second selection marker gene to select a transformed *Aspergillus* microorganism lacking the first and second selection marker genes on its chromosomes.

[105] A method for lacking two types of target genes on chromosomes of a transformed *Aspergillus* microorganism, wherein the method uses first and second selection marker genes available for marker recycling method; among the first and second selection marker genes, one is trpC gene and the other is pyrG gene; a nutritional substance corresponding to the trpC gene is tryptophan and an analogue of tryptophan is 5-FAA; a nutritional substance corresponding to the pyrG gene is uridine and/or uracil and an analogue of uridine and/or uracil is 5-FOA; and the method includes the steps of:

(A) subjecting a transformed *Aspergillus* microorganism lacking the first and second selection marker genes on its chromosomes to homologous recombination targeting the first and second target genes on its chromosomes with the use of a first nucleic acid fragment containing a loop-out region and the first selection marker gene between homologous recombination regions for the first target gene and a second nucleic acid fragment containing a loop-out region and the second selection marker gene between homologous recombination regions for the second target gene, thereby obtaining a transformed *Aspergillus* microorganism; and (B) culturing the transformed *Aspergillus* microorganism obtained in the step (A) in the absence of nutritional substances corresponding to the first and second selection marker genes to select a transformed *Aspergillus* microorganism inserting the first and second selection marker genes on its chromosomes.

[106] The method according to [105] above, further including the step of:

(C) culturing the transformed *Aspergillus* microorganism selected in the step (B) in the presence of a nutritional substance corresponding to the first selection marker gene and an analogue of the nutritional substance as well as a nutritional substance corresponding to the second selection marker gene and an analogue of the nutritional substance to select a transformed *Aspergillus* microorganism lacking the first and second selection marker genes and the first and second target genes on its chromosomes.

[107] The method according to [106] above, wherein the concentration of 5-FAA is 0.005% (w/v) to 0.02% (w/v) and the concentration of 5-FOA is 0.05% (w/v) to 0.15% (w/v).

[108] The method according to any one of [104] to [107] above, wherein the host organism of the transformed *Aspergillus* microorganism is a microorganism of the genus *Aspergillus* different from *Aspergillus aculeatus*, preferably selected from the group consisting of *Aspergillus sojae, Aspergillus oryzae, Aspergillus tamarii, Aspergillus luchuensis, Aspergillus usamii* and *Aspergillus saitoi*.

Effect of the Invention

According to the transformed *Aspergillus* microorganism and method according to one embodiment of the present invention, at least two target genes on chromosomes of the transformed *Aspergillus* microorganism can be efficiently and rapidly deleted by applying marker recycling method. According to the composition and method according to one embodiment of the present invention, a transformed *Aspergillus* microorganism lacking at least two types of selection marker genes available for marker recycling method can be produced. By applying the transformed *Aspergillus* microorganism, composition and method according to one embodiment of the present invention, it is expected to rapidly detect new phenotypes caused by the simultaneous disruption of genes with similar or related structures or functions.

BRIEF DESCRIPTION OF THE DRAWINGS

FIG. 4A shows the results of agarose gel electrophoresis for the selection of the Asparp1-disrupted strain, as described in the examples below.

FIG. 9A shows the results of agarose gel electrophoresis for the selection of the AotrpC-deleted strain, as described in Examples below.

FIG. 9B shows the results of agarose gel electrophoresis for the selection of the AotrpC-deleted strain, as described in Examples below.

FIG. 13A shows the results of agarose gel electrophoresis for the selection of the AspyrG/AstrpC-double-deleted strain, as described in Examples below.

FIG. 13C shows the results of agarose gel electrophoresis for the selection of the AspyrG/AstrpC-double-deleted strain, as described in Examples below.

DESCRIPTION OF EMBODIMENTS

Figure 1:
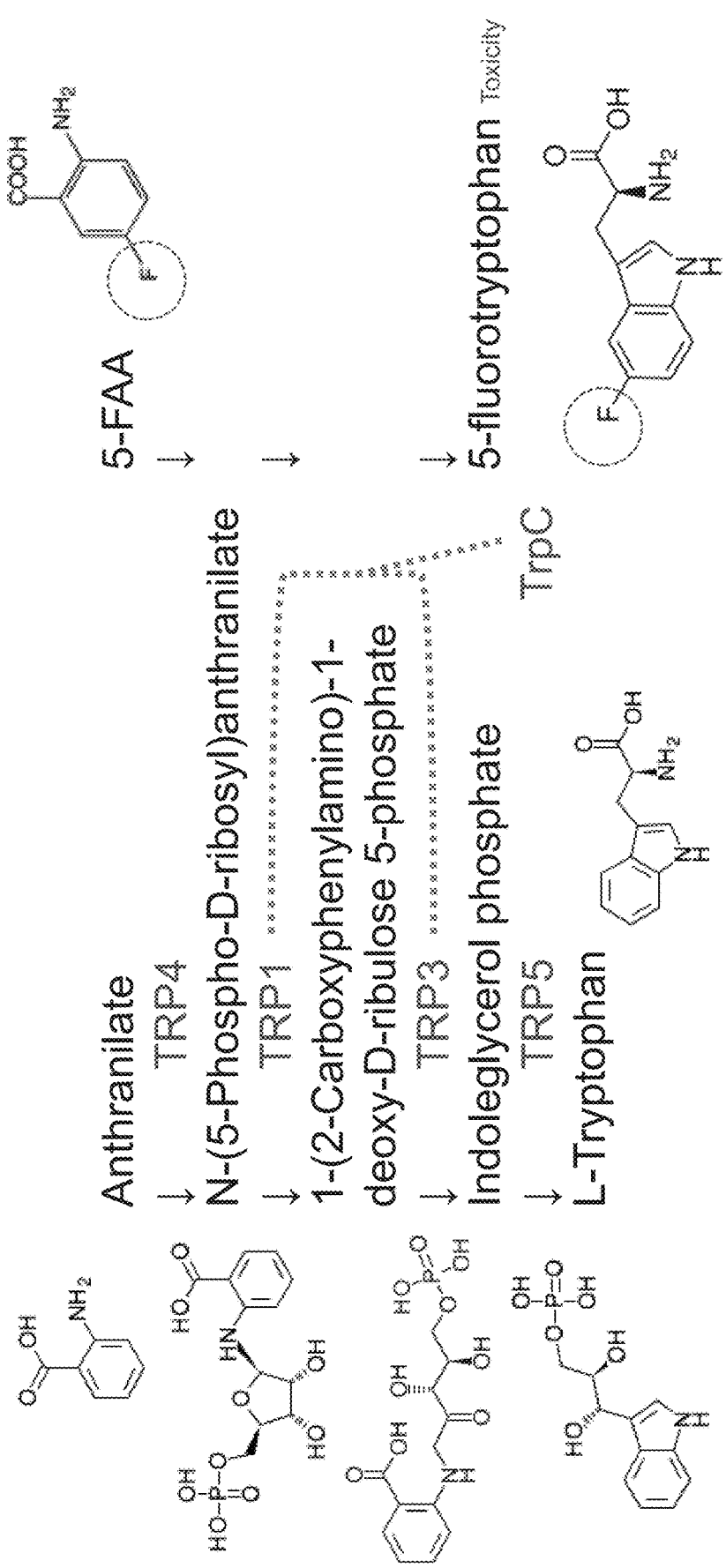
FIG. 1 shows an overview of the tryptophan biosynthesis pathway in yeast.

While the transformed *Aspergillus* microorganism, composition, and method that form one embodiment of the present invention will be now described in detail, the scope of the present invention is not limited only by the description in this section, and the present invention may take various embodiments to the extent that its objective can be achieved.

Unless otherwise specified, each term used herein is used in the meaning commonly used by those skilled in the art and should not be construed to have any meaning that is unduly limiting.

For example, the term "and/or" means any one, or an arbitrary combination of two or more, or a combination of all of a plurality of related items listed.

The term "lack of gene" means that the gene does not function properly and the expression of the gene is hindered due to a partial or total lack of the gene so that the gene is not transcribed properly or the transcribed protein does not perform a function its original protein has. In the description, the lack of gene, the disruption of gene, and the deletion of gene are used synonymously.

The term "expression of gene" means production of a protein encoded by a gene via transcription, translation, and the like, in a form having an original conformation or activity.

The term "selection marker gene" means a gene that brings about a phenotype used as a means of selecting a transformant, and that allows the transformant to be specifically selected or not to be specifically selected in the presence or absence of the corresponding selection substance. The term "function of selection marker gene" means to allow a transformant to be specifically selected in the presence or absence of the corresponding selection substance. For example, if the selection marker gene is a drug resistance gene, the transformant may be specifically selected in the presence of the drug by achieving the function of the selection marker gene. For example, if the selection marker gene is an auxotrophic gene, the transformant may be specifically selected in the absence of the nutritional substance by achieving the function of the selection marker gene. Among the selection marker genes, the "selection marker gene available for marker recycling method" means a selection marker gene that can be used for a counter selection system that makes use of the fact that the expression of the gene prevents a microorganism from growing in an environment containing a certain drug.

The term "homologous recombination regions" mean nucleotide sequences that are homologous to regions on the upstream (at 5' terminus) and the downstream (at 3' terminus) of a gene targeted on chromosomes (target gene). Among the homologous recombination regions, the region on the upstream of the target gene refers to the "homologous recombination upstream region," and the region on the downstream of the target gene refers to the "homologous recombination downstream region."

The term "loop-out" or "looping out" means a phenomenon in which two homologous nucleotide sequences on the same chromosome are homologously recombined and the intervening nucleotide sequences are dropped out. The term "loop-out region" means a region that enables looping out, e.g., a region for removing a selection marker gene which is introduced along with the loop-out region by looping out.

The term "biosynthesis gene" means one, two or more genes that express proteins that function in the biosynthesis pathway of an object substance, e.g., includes a gene that expresses an enzyme that catalyzes a reaction to convert to an object substance.

The term "metabolism gene" means one, two or more genes that express proteins that function in the metabolism pathway of an object substance, e.g., includes a gene that expresses an enzyme that catalyzes a reaction to convert from an object substance to the other substance.

(Outline of Transformed *Aspergillus* Microorganism and Composition)

The transformed *Aspergillus* microorganism according to one embodiment of the present invention relates to a transformed *Aspergillus* microorganism obtained by transforming a host organism in a way to lack two or more types of selection marker genes available for marker recycling method on chromosomes of the host organism, *Aspergillus* microorganism. The composition according to one embodiment of the present invention is used to disrupt a target gene in the transformed *Aspergillus* microorganism according to one embodiment of the present invention, and at least contains two or more types of nucleic acid fragments that contain a loop-out region and a selection marker gene available for marker recycling method between homologous recombination regions.

In the transformed *Aspergillus* microorganism and composition according to one embodiment of the present invention, one, two or more of the selection marker genes available for marker recycling method are a tryptophan biosynthesis gene, and the other one, two or more of the selection marker genes available for marker recycling method are a gene different from tryptophan biosynthesis gene.

(Selection Marker Gene Available for Marker Recycling Method)

The overview of the tryptophan biosynthesis pathway in yeast is shown in FIG. 1. As shown in FIG. 1, the four enzymes are involved in the tryptophan biosynthesis in yeast: TRP4 (anthranilate phosphoribosyltransferase), TRP1 (phosphoribosylanthranilate isomerase), TRP3 (indole-3-glycerol phosphate synthase) and TRP5 (tryptophan synthase). The reaction of chorismate to anthranilate is catalyzed by TRP2 (anthranilate synthase).

In contrast, the present inventors predicted from the public genome database (BioProject Accession: PRJDA60265) of *Aspergillus sojae* (*A. sojae*) NBRC4239 strain that a gene encoding an enzyme corresponding to TRP4 was located in the region 1554760-1553403 of scaffold00063. When attempted to disrupt the region, the present inventors could only obtain mixed strains in which the region on chromosomes was disrupted or not disrupted, and as a result, could not obtain a strain with the region disrupted.

The present inventors predicted that a gene encoding an enzyme corresponding to TRP5 was located in the region 1470936-1473260 of scaffold00060, the region 917953-920152 of scaffold00036, the region 350582-352846 of scaffold00057 and the region 662605-659898 region of scaffold00011. Thus, the present inventors predicted that there were four genes encoding an enzyme corresponding to TRP5, and found it very difficult to disrupt all of them and abandoned the idea.

Furthermore, the present inventors could not find any gene encoding an enzyme corresponding to TRP1 or TRP3 in *A. sojae* NBRC4239 strain. On the other hand, the present inventors predicted that a gene encoding an enzyme that has the both functions of TRP1 and TRP3 in combination was located in the region 1213700-1211376 of scaffold 00048 (DF093577.1), and named this region AstrpC gene. Then, by disrupting the AstrpC gene in *A. sojae*, the present inventors succeeded in obtaining a transformed *Aspergillus* microorganism that is unable to biosynthesize tryptophan from anthranilic acid.

Based on the above background, the tryptophan biosynthesis gene as a selection marker gene available for marker recycling method is preferably the gene encoding the enzyme that has the both functions of TRP1 and TRP3 in combination in yeast, i.e., the trpC gene, but may also be a gene encoding an enzyme corresponding to TRP4, TRP5 or TRP2 in yeast. The tryptophan biosynthesis gene may be used either individually or in combination of two or more of the above genes.

The gene different from tryptophan biosynthesis gene is not particularly limited so long as the gene is a selection marker gene available for marker recycling method that is different from the tryptophan biosynthesis gene, and examples of the gene include drug resistance genes and auxotrophic genes. The auxotrophic genes are not particularly limited so long as the genes complement a nutrient requirement of the host organism, and examples of the genes include pyrG gene, niaD gene, and sC gene. The gene different from tryptophan biosynthesis gene may be used either individually or in combination of two or more of the above genes. In addition, a strain lacking niaD gene shows a phenotype that is resistant to chlorate, and a strain lacking sC gene shows a phenotype that is resistant to selenate.

Each of pyrG gene, trpC gene, niaD gene and sC gene is registered in NCBI GenBank ([URL] https://www.ncbi.nlm.nih.gov/genbank/) for each organism from which the gene is derived. For example, the GenBank accession numbers of pyrG gene, trpC gene, niaD gene and sC gene of *A. sojae*, *A. oryzae* and *A. niger* are listed in Table 1. As for *A. sojae*, the scaffold on the chromosomes is shown. Those skilled in the art can obtain the nucleotide sequences of these genes in *Aspergillus* microorganisms by referring to NCBI GenBank. The version of *A. sojae* scaffold00028 is DF093570.1 and the version of *A. sojae* scaffold00009 is DF093562.1.

TABLE 1

| Gene | Origin of gene | GeneBank Accession no. |
| --- | --- | --- |
| pyrG | *Aspergillus sojae* | scaffold00028; 1770366-1771264 |
| niaD | *Aspergillus sojae* | scaffold00048; 1091779-1088819 |
| sC | *Aspergillus sojae* | scaffold00009; 866277-868468 |
| pyrG | *Aspergillus oryzae* | Y13811.1 |
| trpC | *Aspergillus oryzae* | XM_001727522. 2 |
| niaD | *Aspergillus oryzae* | D49701.1 |
| sC | *Aspergillus oryzae* | AB078786.1 |
| pyrG | *Aspergillus niger* | X06626.1 |
| trpC | *Aspergillus niger* | X07071.1 |
| niaD | *Aspergillus niger* | M77022.1 |
| sC | *Aspergillus niger* | AF538692.1 |

Among the above genes, the gene different from tryptophan biosynthesis gene is preferably an auxotrophic gene in view of the easy selection of transformant. The auxotrophic gene includes biosynthesis genes and metabolic genes. The auxotrophic genes are preferably a gene that complements a requirement for a nutritional substance and is involved in biosynthesizing a toxic substance from an analogue of the nutritional substance, more preferably uracil biosynthesis genes, sulfate metabolic genes and nitrate metabolic genes, still more preferably pyrG gene, niaD gene and sC gene.

The selection marker gene available for marker recycling method may not be completely identical to a gene that is originally retained by a source organism (i.e., wild-type gene). The selection marker gene available for marker recycling method may be DNA that has a nucleotide sequence that hybridizes, under stringent condition, with a nucleotide sequence complementary to a nucleotide sequence of wild-type gene so long as the gene expresses a protein with the enzymatic property that is identical or very similar to that of a protein expressed by a wild-type gene (i.e., wild-type protein).

The term "nucleotide sequence that hybridizes under stringent condition" as used herein means a nucleotide sequence of DNA obtained by hybridization system such as colony hybridization, plaque hybridization and Southern blot hybridization, using DNA having the nucleotide sequence of wild-type gene as a probe.

The term "stringent condition" as used herein refers to a condition specifically distinguished between signals of a specific hybrid and a non-specific hybrid although the condition may vary depending on the hybridization system and the type, sequence, and length of probe to be used. Such condition may be determined by altering hybridization temperature, washing temperature, and salt concentration. For example, if a non-specific hybrid is disadvantageously detected as an intense signal, a hybridization specificity can be increased by elevating hybridization and washing temperatures and optionally lowering salt concentration during washing steps. If even any specific hybrids cannot be detected as a signal, the hybrids can be stabilized by lowering hybridization and washing temperatures and optionally increasing salt concentration during washing steps.

Specific examples of stringent condition include, for example, hybridization performed overnight (for about 8 hours to 16 hours) using a DNA probe as a probe and 5×SSC, 1.0% (w/v) blocking reagent for nucleic acid hybridization (Roche Diagnostics), 0.1% (w/v) N-lauroylsarcosine, and 0.02% (w/v) SDS. Washing is performed twice with 0.1× to 0.5×SSC and 0.1% (w/v) SDS, preferably 0.1×SSC and 0.1% (w/v) SDS for 15 minutes. The hybridization and washing temperatures are 65° C. or more, and preferably 68° C. or more.

DNA having a nucleotide sequence that hybridizes under stringent condition include, for example, DNA identified by performing hybridization under stringent conditions as described above using a filter on which DNA or fragments of the DNA having a nucleotide sequence of wild-type gene derived from a colony or plaque are immobilized; and DNA that can be identified by performing hybridization at a temperature from 40° C. to 75° C. in the presence of 0.5 M to 2.0 M NaCl, preferably at 65° C. in the presence of 0.7 M to 1.0 M NaCl followed by washing the filter with 0.1× to 1×SSC solution (1×SSC solution contains 150 mM sodium chloride and 15 mM sodium citrate) at 65° C. Probe preparation and hybridization techniques can be performed according to methods as described in Molecular Cloning, A Laboratory Manual, 2nd-Ed., Cold Spring Harbor Laboratory, Cold Spring Harbor, NY, 1989; Current Protocols in Molecular Biology, Supplement 1-38, John Wiley & Sons, 1987-1997 (these literatures are also referred to as "technical literatures" hereinafter and are incorporated herein by reference in their entirety). It is understood that those skilled in the art would appropriately determine conditions for obtaining DNA that has a nucleotide sequence hybridizing with a nucleotide sequence complementary to a nucleotide sequences of wild-type gene under stringent condition by taking account of conditions such as salt concentration and temperature of buffers as well as various other conditions including probe concentration, probe length and reaction time.

DNA having a nucleotide sequence that hybridizes under stringent condition include DNA having a particular percentage or higher sequence identity to a nucleotide sequence of DNA having a nucleotide sequence of wild-type gene used as a probe, for example, DNA having 80% or more, preferably 85% or more, more preferably 90% or more, 91% or more, 92% or more, 93% or more, 94% or more, 95% or more, 96% or more, 97% or more, 98% or more, 99% or more, still more preferably 99.5% or more sequence identity to a nucleotide sequence of wild-type gene. The upper limit is not particularly limited, but is typically 100%.

Nucleotide sequences of DNA that hybridize, under stringent condition, with DNA consisting of a nucleotide sequence complementary to a nucleotide sequence of wild-type gene include, for example, nucleotide sequences having one to several, preferably 1 to 20, more preferably 1 to 15, still more preferably 1, 2, 3, 4, 5, 6, 7, 8, 9, or 10 nucleotides deleted, substituted, and/or added per unit in the nucleotide sequence of wild-type gene when 100 nucleotides in a nucleotide sequence are considered as one unit. The term "nucleotide deleted" means a loss or disappearance of a nucleotide in a sequence; the term "nucleotide substituted" means replacement of a nucleotide with another nucleotide in a sequence; the term "nucleotide added" means addition of a new nucleotide inserted into a sequence.

While a protein encoded by a nucleotide sequence that hybridizes with a nucleotide sequence complementary to a nucleotide sequence of wild-type gene under stringent condition may be a protein having an amino acid sequence resulting from deletion, substitution, addition or other modification of 1 to several amino acids in the amino acid sequence of the protein encoded by the nucleotide sequence of the wild-type gene, it has the same activities and/or functions as the protein encoded by the nucleotide sequence of the wild-type gene.

The protein having the activities and/or functions identical or similar to those of the wild-type protein may be a protein that consists of an amino acid sequence having one or several amino acids deleted, substituted, and/or added in the amino acid sequence of the wild-type protein. The range of "one or several amino acids" in the phrase "having one or several amino acids deleted, substituted, and/or added" in the amino acid sequences is not particularly limited, but may mean, for example, 1, 2, 3, 4, 5, 6, 7, 8, 9, 10, 11, 12, 13, 14, 15, 16, 17, 18, 19, or 20, preferably about 1, 2, 3, 4, 5, 6, 7, 8, 9, or 10, and more preferably about 1, 2, 3, 4, or 5 amino acids per unit when 100 amino acids in an amino acid sequence are considered as one unit. As used herein, the term "amino acid deleted" means a loss or disappearance of an amino acid residue in a sequence; the term "amino acid substituted" means replacement of an amino acid residue with another amino acid residue in a sequence; the term "amino acid added" means addition of a new amino acid residue inserted into a sequence.

Specific examples of the "one or several amino acids deleted, substituted, and/or added" include an aspect in which one or several amino acids have been substituted with other chemically similar amino acids. For example, a hydrophobic amino acid may be substituted with another hydrophobic amino acid, or a polar amino acid may be substituted with another polar amino acid having the same charge. Such chemically similar amino acids are known in the art for each amino acid. Specific examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, aspargine, and cysteine. Examples of positively charged basic amino acids include arginine, histidine, and lysine. Examples of negatively charged acidic amino acids include asparatic acid, and glutamic acid.

Examples of the amino acid sequences having deletion, substitution, addition or other modification of one to several amino acids in the amino acid sequence of the wild-type protein include amino acid sequences having a particular percentage or higher sequence identity to the amino acid sequence of the wild-type protein, such as amino acid sequences having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the amino acid sequence of the wild-type protein. The upper limit is not particularly limited, but is typically 100%.

(Means for Calculating Sequence Identity)

While methods for determining sequence identity of nucleotide and amino acid sequences are not particularly limited, the sequence identity can be determined by aligning a nucleotide sequence of a wild-type gene or an amino acid sequence of a protein encoded by a wild-type gene with a nucleotide or amino acid sequence of interest, and using programs that calculate the match rate between the sequences, for example, using generally known methods.

The programs that calculate the match rate between two amino acid sequences or nucleotide sequences include, for example, the algorithm of Karlin and Altschul (Proc. Natl. Acad. Sci. USA 87, 2264-2268, 1990; Proc. Natl. Acad. Sci. USA 90, 5873-5877, 1993, incorporated herein by reference in their entirety) known in the art. BLAST program using this algorithm was developed by Altschul et al. (J. Mol. Biol. 215, 403-410, 1990, incorporated herein by reference in its entirety). Gapped BLAST which determines sequence identity more sensitively than BLAST is also known (Nucleic Acids Res. 25, 3389-3402, 1997, incorporated herein by reference in its entirety). Thus, those skilled in the art can search for sequences having high sequence identity to a given sequence in the database using, for example, the programs as described above. These programs are available, for example, on the website of The National Center for Biotechnology Information (http://blast.ncbi.nlm.nih.gov/Blast.cgi) on the Internet.

While each of the methods as described above can be generally used to search for sequences having sequence identity in the database, Genetyx network version 12.0.1 (Genetyx) can be also used for homology analysis as a means for determining sequence identity of an individual sequence. This method is based on the Lipman-Pearson method (Science 227, 1435-1441, 1985, incorporated herein by reference in its entirety). Upon analysis of sequence identity of nucleotide sequences, regions encoding a protein (CDS or ORF) are used if possible.

(Sources of Selection Marker Gene Available for Marker Recycling Method)

The selection marker gene available for marker recycling method is derived from, for example, biological species in which the expression of selection marker gene available for marker recycling method is found or the function as selection marker gene available for marker recycling method is confirmed. Source organisms of selection marker gene available for marker recycling method include, for example, microorganisms, preferably microorganisms of the genus *Aspergillus* that are same species as or related species to the host organism. Specific examples of the microorganisms of the genus *Aspergillus* include *Aspergillus sojae*, *Aspergillus oryzae*, *Aspergillus niger*, *Aspergillus tamarii*, *Aspergillus luchensis*, *Aspergillus usamii*, *Aspergillus aculeatus*, *Aspergillus saitoi* and *Aspergillus nidulans*.

*Aspergillus sojae*, *Aspergillus oryzae*, *Aspergillus niger*, *Aspergillus tamarii*, *Aspergillus luchensis*, *Aspergillus usamii*, *Aspergillus aculeatus* and *Aspergillus saitoi* listed above as specific examples of the microorganisms of the genus *Aspergillus* have long been used in the production of miso paste, soy sauce, Japanese sake, shochu liquor and other fermented products, as well as in the production of citric acid and enzymes such as amylases. Their high enzyme productivity and high reliability for the safety, backed by a long history of use, make these microorganisms highly useful in industrial applications.

The selection marker gene available for marker recycling method is introduced into a host organism and makes the host organism transformed so that the resulting transformant can express a protein encoded by the selection marker gene available for marker recycling method and can exhibit a different phenotypic trait from the host organism. Therefore, in order that such a protein may be expressed in the transformant and not be inactivated under the growth conditions of the host organism to exert the selection marker activity, the source organism of the selection marker gene available for marker recycling method may be preferably a microorganism of the genus *Aspergillus* that has growth conditions similar to those of the host organism to be transformed.

(Host Organisms)

Host organisms are not particularly limited so long as they are an *Aspergillus* microorganism that has the selection marker genes available for marker recycling method on its chromosomes and that can exert the functions of the selection marker genes by deleting the selection marker genes. The host *Aspergillus* microorganism may be preferably a microorganism of the *Aspergillus* other than *Aspergillus aculeatus*. In terms of the safety and easy culturing, the preferred examples of the host *Aspergillus* microorganism include *Aspergillus sojae, Aspergillus oryzae, Aspergillus niger, Aspergillus tamarii, Aspergillus luchensis, Aspergillus usamii, Aspergillus saitoi* and *Aspergillus nidulans*.

The host organism may be a wild strain or a transformant obtained by transforming a wild strain in advance. The transformant obtained by transforming a wild strain in advance to be used as a host organism is not particularly limited.

Preferably, the *Aspergillus* microorganism that has been transformed to suppress ku gene encoding a protein such as Ku70 and Ku80, which is involved in non-homologous recombination mechanism, may be used for preparing a transformant by homologous recombination because microorganisms of the genus *Aspergillus* tend to have a low frequency of homologous recombination.

Such suppression of ku gene can be achieved by any known method to those skilled in the art. Examples of the method include disruption of ku gene by a ku gene disruption vector and inactivation of ku gene by antisense RNA method using an antisense expression vector for ku gene. It is also possible to disrupt ku gene by genome editing technique using Cas nuclease and guide RNA targeting ku gene. The homologous recombination frequency of the transformed *Aspergillus* microorganism obtained in such a way is markedly increased compared to that of the original *Aspergillus* microorganism which has been not subjected to the genetic manipulation of suppressing ku gene, preferably at least 2 times, preferably at least 5 times, preferably at least 10 times, preferably at least about 50 times that of the original *Aspergillus* microorganism.

One Embodiment of Transformant

One embodiment of the transformant is, but not particularly limited to, a transformed *Aspergillus* microorganism in which the host organism is *Aspergillus sojae, Aspergillus oryzae, Aspergillus niger, Aspergillus tamarii, Aspergillus luchensis, Aspergillus* usamii or *Aspergillus saitoi*; and both pyrG gene and trpC gene on its chromosomes have been deleted.

(Method of producing transformed *Aspergillus* microorganism)

The method of producing a transformed *Aspergillus* microorganism lacking a selection marker gene available for marker recycling method is not particularly limited, and examples of the method include a method including the step of deleting a selection marker gene available for marker recycling method on chromosomes of a host organism according to any known method, or by inserting into or replacing with the locus of the selection marker gene a foreign nucleic acid fragment. The method is preferably carried out using homologous recombination.

The method using homologous recombination may include, for example, the steps of introducing into a host organism a nucleic acid fragment constructed to ligate a foreign nucleic acid fragment between the homologous recombination regions which are homologous to the upstream and downstream regions of the selection marker gene available for marker recycling method on its chromosomes, and replacing the selection marker gene available for marker recycling on its chromosomes with the foreign nucleic acid fragment by homologous recombination. A nucleic acid fragment prepared for transforming a host organism may be referred to herein as a transformation cassette. The foreign nucleic acid fragment is preferably a selection marker gene available for marker recycling method different from the selection marker gene available for marker recycling method to be deleted.

The transformation cassette preferably contains a loop-out region. For example, when in the transformation cassette containing a loop-out region and a foreign nucleic acid fragment, the region having the identical sequence to the loop-out region is present on chromosomes of a host organism in the upstream or downstream of a site that may be inserted by homologous recombination, the transformation cassette is inserted into the chromosome of the host organism by homologous recombination and then homologous recombination occurs between the loop-out region and the region homologous to the loop-out region placed at the upstream or downstream of the loop-out region so that the introduced foreign nucleic acid fragment can be removed due to looping out. By taking measures as described above, it is possible to obtain the transformant in which the foreign nucleic acid fragment is introduced into the locus of the selection marker gene followed by being removed.

One embodiment of the transformation cassette is, for example, a nucleic acid fragment that contains a loop-out region and a foreign nucleic acid fragment between homologous recombination regions. The nucleic acid fragment may be obtained by obtaining a DNA fragment of the homologous recombination upstream region, a DNA fragment of the loop-out region, and a DNA fragment of the homologous recombination downstream region by executing polymerase chain reaction (referred to hereinafter as PCR) using a chromosomal DNA of the *Aspergillus* microorganism as a template according to any known method; preparing a plasmid vector for construction by ligating the homologous recombination upstream region, the loop-out region, the foreign nucleic acid (DNA) fragment, and the homologous recombination downstream region in sequence into In-Fusion Cloning Site in the multi-cloning site of plasmid pUC19; and then amplifying the resulting plasmid for construction as a template DNA by PCR.

Methods for extracting a chromosomal DNA are not particularly limited, and examples of the methods include a method including the steps of culturing *Aspergillus* microorganism; dehydrating the collected microorganism; physically triturating the dehydrated microorganism using a mortar while chilled in liquid nitrogen to form fine-powder-like cells debris; and then extracting a fraction containing a chromosomal DNA from the cells debris using a standard technique. A commercially available DNA extraction kit such as DNeasy Plant Mini Kit (Qiagen) may be used to extract a chromosomal DNA.

Methods for transforming an *Aspergillus* microorganism may be properly selected from any known methods to those skilled in the art, and examples of the methods include PEG-mediated protoplast transformation in which protoplasts of a host organism are prepared and polyethylene glycol and calcium chloride are added (See, for example, Mol. Gen. Genet. 218, 99-104, 1989, Japanese Unexamined Patent Application Publication No. 2007-222055; incorporated herein by reference in its entirety). The medium to regenerate the transformant may be properly selected depending on the host organism used, the selection marker gene deleted and the foreign nucleic acid fragment introduced. For example, when *Aspergillus sojae* is used as a host organism and the drug resistance gene is used as a foreign nucleic acid fragment, the transformant may be regenerated in, for example, the minimal agar medium containing the corresponding drug.

The occurance of a transformed *Aspergillus* microorganism lacking a selection marker gene available for marker recycling method may be confirmed by culturing the transformant under conditions that allow the function of the deleted selection marker gene available for marker recycling method to be exerted; and observing the growth. For example, if the deleted selection marker genes available for marker recycling method are the trpC and pyrG genes, it is confirmed that the transformed *Aspergillus* microorganism is produced when the growth of the transformant in the presence of 5-fluoroanthranilic acid (5-FAA) and 5-fluoroorotic acid (5-FOA) is observed.

The occurance of the transformed *Aspergillus* microorganism may be also confirmed by the following procedure: a chromosomal DNA is extracted from the transformant and PCR is performed using the chromosomal DNA as a template to detect the presence of a PCR product that can be amplified if the transformation has occurred.

For example, when the transformation is carried out by homologous recombination, it is preferred to perform PCR using a forward primer complementary to a region located at the upstream of the homologous recombination upstream region ligated into a transformation cassette with a reverse primer complementary to a region located at the downstream of the homologous recombination downstream region ligated into a transformation cassette; and then to determine whether a PCR product having a length as expected when the homologous recombination has occurred is amplified.

The transformant lacking two types of selection marker genes available for marker recycling method can be produced by deleting the second selection marker gene available for marker recycling method in the transformant lacking the first selection marker gene available for marker recycling method. By repeating this procedure, a transformant lacking several types of selection marker genes available for marker recycling method can be produced.

For example, if the selection marker genes available for marker recycling method are the trpC and pyrG genes, the transformed *Aspergillus* microorganism lacking the trp C and pyrG genes can be obtained by transforming the transformed *Aspergillus* microorganism lacking the pyrG gene as a host organism so as to delete the trpC gene using a transformation cassette containing a loop-out region and the pyrG gene between the homologous recombination regions; and further removing the introduced pyrG gene by looping out. Examples of the transformed *Aspergillus* microorganism lacking the pyrG gene include *Aspergillus sojae* KP-del strain as described in Example 2 of Japanese Patent No. 6261039 (incorporated herein by reference in its entirety).

Examples of the methods for producing a transformed *Aspergillus* microorganism include, but are not limited to, the method as described in Example 2 of Japanese Patent No. 6261039. According to the method, a strain in which the auxotrophic gene is inactivated by spontaneous mutation is obtained from a wild strain of *Aspergillus* microorganism. The auxotrophic gene may or may not be a selection marker gene available for marker recycling method to be deleted.

If the auxotrophic gene is a selection marker gene available for marker recycling method to be deleted, the transformed *Aspergillus* microorganism lacking the two types of selection marker genes available for marker recycling method on its chromosomes can be obtained by introducing the auxotrophic gene into the locus of a tryptophan biosynthesis gene to delete the tryptophan biosynthesis gene on its chromosomes followed by removing the auxotrophic gene by looping out.

If the auxotrophic gene is a gene different from a selection marker gene available for marker recycling method to be deleted, the transformed *Aspergillus* microorganism lacking the two types of selection marker genes available for marker recycling method on its chromosomes can be obtained by introducing the auxotrophic gene into the locus of a selection marker gene available for marker recycling method different from tryptophan biosynthesis gene to delete the selection marker gene; introducing the selection marker gene into the locus of a tryptophan biosynthesis gene to delete the tryptophan biosynthesis gene; and then removing the introduced selection marker gene by looping out. For example, the transformed *Aspergillus* microorganism lacking the two types of selection marker genes available for marker recycling method on its chromosomes can be obtained by introducing the auxotrophic gene into the locus of a tryptophan biosynthesis gene to delete the tryptophan biosynthesis gene; introducing the tryptophan biosynthesis gene into the locus of a selection marker gene available for marker recycling method different from the tryptophan biosynthesis gene to delete the selection marker gene; and then removing the introduced tryptophan biosynthesis gene by looping out.

Another aspect of the present invention is a method of producing a transformed *Aspergillus* microorganism according to one embodiment of the present invention. The production method according to one embodiment of the present invention includes at least the following steps (1) to (3), but among the first and second selection marker genes available for maker recycling method, one is a tryptophan biosynthesis gene and the other is a gene that complements a requirement for a nutritional substance and is involved in biosynthesizing a toxic substance from an analogue of the nutritional substance:

(1) subjecting a transformed *Aspergillus* microorganism lacking the first selection marker gene available for maker recycling method on its chromosomes to homologous recombination targeting the second selection marker gene available for maker recycling method on its chromosomes with the use of a nucleic acid fragment containing a loop-out region and the first selection marker gene between homologous recombination regions, thereby obtaining a transformed *Aspergillus* microorganism;

(2) culturing the transformed *Aspergillus* microorganism obtained in the step (1) in the presence of the nutritional substance corresponding to the second selection marker gene to select a transformed *Aspergillus* microorganism inserting the first selection marker gene on its chromosomes and lacking the second selection marker gene on its chromosomes; and (3) culturing the transformed *Aspergillus* microorganism selected in the step (2) in the presence of a nutritional substance corresponding to the first selection marker gene and an analogue of the nutritional substance as well as the nutritional substance corresponding to the second selection marker gene to select a transformed *Aspergillus* microorganism lacking the first and second selection marker genes on its chromosomes.

(Method for Lacking Target Genes)

The use of the transformed *Aspergillus* microorganism according to one embodiment of the present invention can allow at least two types of target genes on its chromosomes of the transformed *Aspergillus* microorganism to be removed simultaneously or in a stepwise manner.

Another aspect of the present invention is a method of lacking two types of target genes on chromosomes of the transformed *Aspergillus* microorganism according to one embodiment of the present invention. The method for lacking target genes according to one embodiment of the present invention includes at least the following steps (A) and (B), but among the first and second selection marker genes available for maker recycling method, one is a tryptophan biosynthesis gene and the other is a gene that complements a requirement for a nutritional substance and is involved in biosynthesizing a toxic substance from an analogue of the nutritional substance.

(A) subjecting a transformed *Aspergillus* microorganism lacking the first and second selection marker genes for maker recycling method on its chromosomes to homologous recombination targeting the first and second target genes on its chromosomes with the use of a first nucleic acid fragment containing a loop-out region and the first selection marker gene between homologous recombination regions for the first target gene and a second nucleic acid fragment containing a loop-out region and the second selection marker gene between homologous recombination regions for the second target gene, thereby obtaining a transformed *Aspergillus* microorganism; and (B) culturing the transformed *Aspergillus* microorganism obtained in the step (A) in the absence of nutritional substances corresponding to the first and second selection marker genes to select a transformed *Aspergillus* microorganism inserting the first and second selection marker genes on its chromosomes.

The method for lacking target genes according to one embodiment of the present invention preferably further includes the following step (C):

(C) culturing the transformed *Aspergillus* microorganism selected in the step (B) in the presence of the nutritional substance corresponding to the first selection marker gene and the analogue of the nutritional substance as well as the nutritional substance corresponding to the second selection marker gene and the analogue of the nutritional substance, thereby selecting a transformed *Aspergillus* microorganism lacking the first and second selection marker genes and the first and second target genes on its chromosomes.

If two or more types of target genes on chromosomes of a transformed *Aspergillus* microorganism are to be deleted in a stepwise manner, the above steps (A) to (C) may be conducted with the use of the first nucleic acid fragment for the first target gene, the nutritional substance corresponding to the first selection marker gene available for marker recycling method and the analog of the nutritional substance, and the nutritional substance corresponding to the second selection marker gene; and then the above steps (A) to (C) may be conducted with the use of the second nucleic acid fragment for the second target gene, the nutritional substance corresponding to the second selection marker gene and the analog of the nutritional substance, and the nutritional substance corresponding to the first selection marker gene. The step (C) can also be carried out in stages, dividing the step into two steps: one is to remove the first selection marker gene and the other is to remove the second selection marker gene. Such a stepwise method for lacking target genes is also encompassed in the method for lacking target genes according to one embodiment of the present invention.

(Specific Examples of Methods)

In a non-limiting specific example of the production method according to one embodiment of the present invention and the method for lacking target genes according to one embodiment of the present invention, the first selection marker gene available for marker recycling method is pyrG gene; the nutritional substance corresponding to the first selection marker gene is uracil/uridine; the analog of the nutritional substance corresponding to the first selection marker gene is 5-FOA; the second selection marker gene available for marker recycling method is trpC gene; the nutritional substance corresponding to the second selection marker gene is tryptophan; and the analog of the nutritional substance corresponding to the second selection marker gene is 5-FAA.

In a non-limiting specific example of the production method according to one embodiment of the present invention and the method for lacking target genes according to one embodiment of the present invention, the first selection marker gene available for marker recycling method is trpC gene; the nutritional substance corresponding to the first selection marker gene is tryptophan; the analog of the nutritional substance corresponding to the first selection marker gene is 5-FAA; the second selection marker gene available for marker recycling method is pyrG gene; the nutritional substance corresponding to the second selection marker gene is uracil/uridine; and the analog of the nutritional substance corresponding to the second selection marker gene is 5-FOA.

In the above specific examples, it was first discovered by the present inventors that the different concentrations of 5-FAA and 5-FOA are used in accordance with each selection of the following strains: a strain resistant to 5-FAA, a strain resistant to 5-FOA, and a strain resistant to both 5-FAA and 5-FOA. The concentrations of 5-FAA and 5-FOA used in the selection of the strain resistant to both 5-FAA and 5-FOA are preferably smaller than each concentration of 5-FAA or 5-FOA used in the selection of the strain resistant to 5-FAA or the strain resistant to 5-FOA. For the selection of the strain resistant to 5-FAA, 5-FAA is preferably used in the range between 0.03% (w/v) and 0.05% (w/v). For the selection of the strain resistant to 5-FOA, 5-FOA is preferably used in the range between 0.2% (w/v) and 0.4% (w/v). For the selection of the strain resistant to both 5-FAA and 5-FOA, 5-FAA is preferably used in the range between 0.005% (w/v) and 0.02% (w/v) while 5-FOA is preferably used in the range between 0.05% (w/v) and 0.15% (w/v).

The target genes in the method for lacking target genes according to one embodiment of the present invention are not limited, and may be appropriately determined depending on the purpose of the research or investigation. For example, as described in Examples below, if the host organism is *Aspergillus sojae*, the target genes may be parp1 gene and nph gene, and a double-disrupted strain in which these genes have been disrupted can be obtained.

In addition, by applying the method for lacking target genes according to one embodiment of the present invention, the use of two types of selection marker genes available for marker recycling method may make it possible to achieve something that cannot be achieved by using only one type of selection marker gene available for marker recycling method. For example, by introducing trpC gene into the locus of ku gene of a transformed *Aspergillus* microorganism lacking pyrG and trpC genes, a ku-disrupted strain can be produced. In this case, not only a nucleic acid fragment containing trpC gene between the homologous recombination regions but also two types of nucleic acid fragments splitting the fragment in a way that partially overlap each other in the middle of trpC gene can be prepared and used for ku gene disruption. Then, after introducing and removing pyrG gene into the locus of a protease gene as a target gene, and optionally repeat the step of introducing and removing pyrG gene into the locus of another protease gene, the introduced trpC gene is removed to restore the ku gene. In this case, by partially overlapping the ku gene, it is possible to remove the trpC gene and restore the ku gene by looping out. By randomly introducing multiple copies of a gene expression cassette expressing the desired protein into the obtained protease gene-disrupted strain by non-homologous recombination, a strain that expresses the protein at high levels by preventing its degradation by the protease can be obtained.

In the production method according to one embodiment of the present invention and the method for lacking target genes according to one embodiment of the present invention, various steps or operations can be added at the former stage or the latter stage of the above-mentioned step or in the step so long as the objectives of the present invention can be achieved.

The present invention will now be described in further detail with reference to the following Examples, which are not intended to limit the present invention. The present invention may take various forms to the extent that the objectives of the present invention are achieved.

EXAMPLES

The primers used in Examples are shown in Table 2A and Table 2B. In addition, in the tables, lower-case sequences represent additional sequences for ligating into adjacent fragments.

[TABLE 2A]

| SEQ ID No. | Name of primer | Type of primer | Region to be amplified | Sequence (5' →3') |
|---|---|---|---|---|
| 1 | TrpC_-2060F_pUC | Forward | As upstream region 1 | cggtacccggggatc ATGTGGAGCCAACTT TGGTAGCGA |
| 2 | TrpC_-54R_pyrG | Reverse | As upstream region 1 | tagcaataagcccaa TGCGTGAGAATCGTA AGCGCAG |
| 3 | PyrG_-407F | Forward | AspyrG | TTGGGCTTATTGCTA TGTCCCTGAAAGG |
| 4 | PyrG_1431R | Reverse | AspyrG | CCGCACCTCAGAAGA AAAGGATGA |
| 5 | TrpC_2424F_pyrG | Forward | As downstream region 1 | tcttctgaggtgcgg TCTACACCTCAATTT CGGGCTGCA |
| 6 | TrpC_3923R_pUC | Reverse | As downstream region 1 | cgactctagaggatc AAAAACTCGACGAAG CTGCTGC |
| 7 | TrpC_-2060F | Forward | AstrpC disruption cassette | ATGTGGAGCCAACTT TGGTAGCGA |
| 8 | TrpC_3923R | Reverse | AstrpC disruption cassette | AAAAACTCGACGAAG CTGCTGC |
| 9 | TrpC_180F | Forward | Region for inserting AstrpC disruption cassette | GGACGAATTGATCGC CAAGAAGCCGA |
| 10 | TrpC_871R | Reverse | Region for inserting AstrpC disruption cassette (in AstrpC disruption region) | TGTTGAGGTCGTAAG CAGCCTGAAG |
| 11 | Lig1_85F | Forward | Aslig1 (PCR control) | ATCAGCTGTCGTGCT TGTGTCCCA |
| 12 | Lig1_523R | Reverse | Aslig2 (PCR control) | CCAACCCCATTAGAA GCCTGTCCATC |
| 13 | TrpC_-2118F | Forward | Upper region than As upstream region 1, and lower region than As downstream region 1 | ATGAGATCCAGGAGC ACCGTTCGA |

[TABLE 2A]-continued

| SEQ ID No. | Name of primer | Type of primer | Region to be amplified | Sequence (5'→3') |
|---|---|---|---|---|
| 14 | TrpC_4240R | Reverse | Upper region than As upstream region 1, and lower region than As downstream region 1 | TTGGCGCTTAAGGTG TTGGAAGG |
| 15 | PARP1_-1910F_pUC | Forward | As upstream region 2 | cggtacccggggatc TCTAATGCAAACATT GCGGCTGAG |
| 16 | PARP1_-10R | Reverse | As upstream region 2 | TGAATCCAGTGATGG ACAATGCGA |
| 17 | PARP1_2341F_-24F | Forward | As loop-out region 1 | ccatcactggattca TGAGATAATTGCTGG GCGGTCCT |
| 18 | PARP1_3338R_Trp | Reverse | As loop-out region 1 | aaagctgtatcttcc TTAAGGCATATCGCT CCGCGACCT |
| 19 | TrpC_-391F | Forward | AstrpC | GGAAGATACAGCTTT TATGCGCAGGT |
| 20 | TrpC_3067R | Reverse | AstrpC | CCGTTTTGGTGTCCG ATTACGGGA |
| 21 | PARP1_214F_Trp | Forward | As downstream region 2 | cggacaccaaaacgg TGTGACTACCCAGAG AGAGGTGGA |
| 22 | PARP1_2320R_pUC | Reverse | As downstream region 2 | cgactctagaggatc TTCTGGCGGATCTGA GCAACATCG |
| 23 | PARP1_-1910F | Forward | Asparp1 disruption cassette | TCTAATGCAAACATT GCGGCTGAG |
| 24 | PARP1_2320R | Reverse | Asparp1 disruption cassette | TTCTGGCGGATCTGA GCAACATCG |
| 25 | PARP1_123F | Forward | Region for inserting AstrpC disruption cassette (in Asparp1 disruption region) | GCTATTTTGGGGTTG CAGCGGATG |
| 26 | PARP1_582R | Reverse | Region for inserting AstrpC disruption cassette | TGGAACTCTCCTCGC TGACATCA |
| 27 | Ptef_-718F | Forward | Ptef (PCR control) | CCACAACTGCTTGGG TTTTGACC |
| 28 | Ptef_-1R_2 | Reverse | Ptef (PCR control) | TTTGAAGGTGGTGCG AACTTTG |
| 29 | PARP1_-1958F | Forward | Upper region than As upstream region 2, and lower region than As downstream region 2 | TCCGCAATGGATTTA GGTTGGTTCG |
| 30 | PARP1_3368R | Reverse | Upper region than As upstream region 2, and lower region than As downstream region 2 | GTCGACATTCATACT GCGCCTTCTCA |
| 31 | AoTrpC_-2058F_pUC | Forward | Ao upstream region 1 | cggtacccggggatc ATGTAGAGCCAACTT TGGTAGCGA |
| 32 | AoTrpC_-84R_pyrG | Reverse | Ao upstream region 1 | tagcaataagcccaa CTATCGACTAAGCAG CGACCCTAAC |

[TABLE 2A]-continued

| SEQ ID No. | Name of primer | Type of primer | Region to be amplified | Sequence (5'→3') |
|---|---|---|---|---|
| 33 | AoTrpC_2356F_pyrG | Forward | Ao downstream region 1 | tcttctgaggtgcgg CAACTTGTCACAGAT CCGGACGATG |
| 34 | AoTrpC_3920R_pUC | Reverse | Ao downstream region 1 | cgactctagaggatc ACTCGACTGAAGCTG CTACTTCCAG |
| 35 | AoTrpC_-2058F | Forward | AotrpC disruption cassette | ATGTAGAGCCAACTT TGGTAGCGA |
| 36 | AoTrpC_3920R | Reverse | AotrpC disruption cassette | ACTCGACTGAAGCTG CTACTTCCAG |
| 37 | AoLig1_464F | Forward | Aolig1 (PCR control) | GCGAAATCAGCGACA CCACACGA |
| 38 | AoLig1_925R | Reverse | Aolig2 (PCR control) | TGTAGCCTGCACCTT TTCCATGGTC |
| 39 | AoTrpC_2116F | Forward | Upper region than Ao upstream region 1, and lower region than Ao downstream region 1 | ATGAGATCCAGAAGC ACCGTTCGA |
| 40 | AoHypG_-775F_pUC | Forward | Ao upstream region 2 | cggtacccggggatc GTTGATGACGGCAGG TTTTCCGTT |
| 41 | AoHypG_732R_TrpC | Reverse | Ao upstream region 2 | aaagctgtatctttc CTTGAAGCCAACCCA GGAGACGAAG |
| 42 | AoTrpC_-390F | Forward | AotrpC | GAAAGATACAGCTTT TATGCGCAGGT |
| 43 | AoHypG_-1794F_TrpC | Forward | Ao loop-out region 1 | cggacaccaaaacgg CGAAGCCGTGCAGCC TATAGTTCC |
| 44 | AoHypG_-817R_813R | Reverse | Ao loop-out region 1 | tacgtcgattacccc TGTACAGGACATGGA AACCGCTGAA |
| 45 | AoHypG_799F | Forward | Ao downstream region 2 | GGGGTAATCGACGTA CAGGACTTGG |
| 46 | AoHypG_2296R_pUC | Reverse | Ao downstream region 2 | cgactctagaggatc AACCCGGCCCATTTC TACGAAGAG |
| 47 | AoHypG_-775F | Forward | AohypG disruption cassette | GTTGATGACGGCAGG TTTTCCGTT |
| 48 | AoHypG_2296R | Reverse | AohypG disruption cassette | AACCCGGCCCATTTC TACGAAGAG |
| 49 | AoHypG_741F | Forward | Region for inserting AohypG disruption cassette | ATGCTGTGCCTACGG GTAATTAGGGA |
| 50 | AoHypG_1442R | Reverse | Region for inserting AohypG disruption cassette (in AohypG disruption region) | GATTTGGCCGGTACG ACTCTCGTT |
| 51 | AoHypG_-1942F | Forward | Upper region than Ao upstream region 2, and lower region than Ao downstream region 2 | CGACCTGGATCTGCG ATGTCGTTG |
| 52 | AoHypG_2339R | Reverse | Upper region than Ao upstream region 2, and lower region than Ao downstream region 2 | CGTTCAGCGAAGACA GGCAGCAAC |

[TABLE 2A]-continued

| SEQ ID No. | Name of primer | Type of primer | Region to be amplified | Sequence (5'→3') |
|---|---|---|---|---|
| 53 | AnTrpC_-1890F_pUC | Forward | An upstream region 1 | cggtacccggggatcGGAATTGCTCCAACTCTCGGCTTTC |
| 54 | AnTrpC_-76R_pyrG | Reverse | An upstream region 1 | tagcaataagcccaaAGGGCAATGCACATAGAAACACAC |
| 55 | AnTrpC_2340F_pyrG | Forward | An downstream region 1 | tcttctgaggtgcggGCATGGGATTTAAGGGCATCATTGG |
| 56 | AnTrpC_4110R_pUC | Reverse | An downstream region 1 | cgactctagaggatcACTTCCTGGCCTCTCATCATTCGCA |
| 57 | AnTrpC_-1890F | Forward | AntrpC disruption cassette | GGAATTGCTCCAACTCTCGGCTTTC |
| 58 | AnTrpC_4110R | Reverse | AntrpC disruption cassette | ACTTCCTGGCCTCTCATCATTCGCA |
| 59 | AnTrpC_842F | Forward | AntrpC | TCCAGGCTGCCTATGACCTTAACCTG |
| 60 | AnTrpC_1261R | Reverse | AntrpC(in AntrpC disruption region) | GGCTACGGGAGTAGTGATACAACCGA |

[Table 2B]

| SEQ ID No. | Name of primer | Type of primer | Region to be amplified | Sequence (5'→3') |
|---|---|---|---|---|
| 61 | pyrG_8F | Forward | AspyrG | CCAAGTCGCAATTGACCTACAGCGCA |
| 62 | pyrG_869R | Reverse | AspyrG (in AspyrG) | ATCCCATCCCTCTTTCTGGTACCGCT |
| 63 | AnTrpC_-1961F | Forward | Upper region than An upstream region 1, and lower region than An downstream region 1 | CAAAGTGATCTCCGAGGCTTTGGATG |
| 64 | AnTrpC_4161R | Reverse | Upper region than An upstream region 1, and lower region than An downstream region 1 | CAGAATCTCTACGTCCGAACCAGTCA |
| 65 | AnTpsC_-2148F_pUC | Forward | An upstream region 2 | cggtacccggggatcTCCGATCTTCCTTCTCATCACCCTT |
| 66 | AnTpsC_-294R | Reverse | An upstream region 2 | GCCTGGTTATGTTGGATGTGTCAAG |
| 67 | AnTpsC_2673F_-308F | Forward | An loop-out region 1 | ccaacataaccaggcGATCCCTAAACATGACCAGCTTCAG |

[Table 2B]-continued

| SEQ ID No. | Name of primer | Type of primer | Region to be amplified | Sequence (5'→3') |
|---|---|---|---|---|
| 68 | AnTpsC_3668R_TrpC | Reverse | An loop-out region 1 | catcgagcaactaga CCATACGTCAGATGC ATCGCCGTAA |
| 69 | AnTrpC_-455F | Forward | AntrpC | TCTAGTTGCTCGATG TGATGCGAA |
| 70 | AnTrpC_2749R | Reverse | AntrpC | GGGAGAGGTAAAGAT TCCAGTGGATG |
| 71 | AnTpsC_688F_TrpC | Forward | An downstream region 2 | atctttacctctccc TGCTTTGTGCGGAGT CTCTGTAGG |
| 72 | AnTpsC_2544R_pUC | Reverse | An downstream region 2 | cgactctagaggatc ATACATCTCGTGTTG GGCAAGACAG |
| 73 | AnTpsC_-2148F | Forward | AohypG disruption cassette | TCCGATCTTCCTTCT CATCACCCTT |
| 74 | AnTpsC_2544R | Reverse | AohypG disruption cassette | ATACATCTCGTGTTG GGCAAGACAG |
| 75 | AnTpsC_65F | Forward | AntpsC | GGGGATACGAATCTT CCCTCTCCAGT |
| 76 | AnTpsC_494R | Reverse | AntpsC (in AntpsC disruption region) | GTAATCGTGCACCCA GATCAATGACC |
| 77 | AnTpsC_-2173F | Forward | Upper region than An upstream region 2, and lower region than An downstream region 2 | GACAGGAATCGGAAA AGTCCGCATCT |
| 78 | AnTpsC_3730R | Reverse | Upper region than An upstream region 2, and lower region than An downstream region 2 | TCGAACTACTGGAAG ACTGCACCTTCT |
| 79 | TrpC_-54R | Forward | Plasmid pTrpC_HR | TGCGTGAGAATCGTA AGCGCAG |
| 80 | PyrG_-407F | Reverse | Plasmid pTrpC_HR | TTGGGCTTATTGCTA TGTCCCTGAAAGG |
| 81 | TrpC_4219F_-68F | Forward | As loop-out region 2 | tacgattctcacgca CTTCCAACACCTTAA GCGCCAAGA |
| 82 | TrpC_5523R_pyrG | Reverse | As loop-out region 2 | tagcaataagcccaa CACCGTAAAGCCTAA TGAGGGTGAA |
| 83 | TrpC_6040R | Reverse | Upper region than As upstream region 1, and lower region than As downstream region 1 | GTCATCCCCATTATC CGAGCCATCA |

[Table 2B]-continued

| SEQ ID No. | Name of primer | Type of primer | Region to be amplified | Sequence (5'→3') |
|---|---|---|---|---|
| 84 | NpH_-2217F_pUC | Forward | As upstream region 3 | cggtacccggggatc ATGGAACTGACGTCC TTGAGGCGT |
| 85 | NpH_-121R | Reverse | As upstream region 3 | ACGTTGAATTGCCTT TCAGTCACCCCT |
| 86 | NpH_2312F_-135F | Forward | As loop-out region 3 | aaggcaattcaacgt TGTCGGGTTTCCATA AGGACGAGGA |
| 87 | NpH_3469R_pyrG | Reverse | As loop-out region 3 | tagcaataagcccaa ATGATGCGGTGGCAT TCAAGCCGA |
| 88 | NpH_223F_pyrG | Forward | As downstream region 3 | tcttctgaggtgcgg TTCCGCAATGGTATG CTCCCGATC |
| 89 | NpH_2265R_pUC | Reverse | As downstream region 3 | cgactctagaggatc ACCAAGGATTCACCC ACCTTGCTC |
| 90 | NpH_-2217F | Forward | Asnoh disruption cassette | ATGGAACTGACGTCC TTGAGGCGT |
| 91 | NpH_2265R | Reverse | Asnph disruption cassette | ACCAAGGATTCACCC ACCTTGCTC |
| 92 | NpH_-69F | Forward | Region for Inserting Asnph disruption cassette | ACTCCATCACAAACA GGTCATTCG |
| 93 | NpH_222R | Reverse | Region for Inserting Asnph disruption cassette (in Asnph disruption region) | CAGAGACACTTTCTG CACCGGA |
| 94 | NpH_2381F | Forward | Upper region than As upstream region 3, and lower region than As downstream region 3 | GGCTTGATTGATGCG ACGAGACAGT |
| 95 | NpH_3494R | Reverse | Upper region than As upstream region 3, and lower region than As downstream region 3 | ACGAACTGGGTGTAT GAGGGTGGTGA |

Example 1: Use of trpC Gene as a Selection Marker Gene Available for Marker Recycling Method in *Aspergillus sojae*

1. Preparation of AstrpC-Disrupted Strain
(1-1) Extraction of Chromosomal DNA

In a 150 ml Erlenmeyer flask, 30 mL of polypeptone-dextrin medium (containing 1% (w/v) polypeptone, 2% (w/v) dextrin, 0.5% (w/v) KH2PO4, 0.1% (w/v) NaNO$_3$, 0.05% (w/v) MgSO$_4$.7H$_2$O, 0.1% (w/v) casamino acids; pH 6.0) was prepared with distilled water. The medium was inoculated with the conidia of *Aspergillus sojae* NBRC4239 strain and was subjected to shake culture overnight at 30° C.

The cells were collected from the resulting culture broth by filtration and were placed between sheets of paper towel to remove moisture. The cells were then triturated using a liquid nitrogen-chilled mortar and pestle while being chilled in liquid nitrogen. Using DNeasy Plant Mini Kit (Qiagen), the chromosomal DNA was extracted from the resulting triturated cells.

(1-2) Preparation of Plasmid Containing AstrpC Disruption Cassette

In the following manner, prepared was a plasmid construct in which an upstream region 1 for homologous recombination (As upstream region 1), pyrG gene as a transformation marker complementary to uridine/uracil requirement, and a downstream region 1 for homologous recombination (As downstream region 1) were ligated into pUC19 in sequence.

In order to amplify the As upstream region 1, the AspyrG gene and the As downstream region 1, PCR was performed using the chromosomal DNA of *A. sojae* NBRC4239 obtained in the (1-1) above to serve as a template DNA, Q5 Hot Start High-Fidelity 2× Master Mix (New England Biolabs) to serve as a PCR enzyme, and T100 thermal cycler (BIO RAD) to serve as a PCR device. The PCR was performed according to the protocol provided with the enzyme.

Primers used to amplify the As upstream region 1, the AspyrG gene and the As downstream region 1 are the primers of SEQ ID NOs: 1 to 6. The amplified DNA fragments were purified using QIAquick PCR Purification Kit (Qiagen).

The pUC19 used was pUC19 linearized Vector provided with In-Fusion HD Cloning Kit (Clontech). Using the In-Fusion HD Cloning Kit, the amplified three types of DNA fragments were ligated into pUC19 at In-Fusion Cloning Site located in the multiple cloning site according to the protocols provided with the kit, thereby obtaining a plasmid construct.

The resulting plasmid construct was used to transform competent cells ECOS Competent *Escherichia coli* JM109 (Nippon Gene) in accordance with the manufacturer's instructions to obtain a transformed *E. coli*.

The resulting transformed *E. coli* was then subjected to shake culture overnight at 37° C. in an LB liquid medium containing 50 μg/ml ampicillin. After the culture period, the culture broth was centrifuged to collect cells. Using Fast-Gene Plasmid Mini Kit (Nippon Genetics), A plasmid DNA was extracted from the collected cells according to the protocols provided with the kit.

Such a plasmid was obtained in which the sequences of [As upstream region 1]-[AspyrG]-[As downstream region 1] in sequence were ligated into pUC19 at the multiple cloning site. The resulting plasmid was referred to as pTrpC_HR.

(1-3) Amplification of AstrpC Disruption Cassette

Using the plasmid pTrpC_HR obtained in (1-2) above to serve as a template DNA, the AstrpC disruption cassette was obtained by carrying out PCR and purification of the PCR product according to the description in (1-2) above. Primers used are the primers of SEQ ID NOs: 7 to 8.

As such, the AstrpC disruption cassette was obtained in which the sequences of [As upstream region 1]-[AspyrG]-[As downstream region 1] were ligated in sequence.

(1-4) Transformation of *Aspergillus sojae* KP-Del Strain

Figure 2:
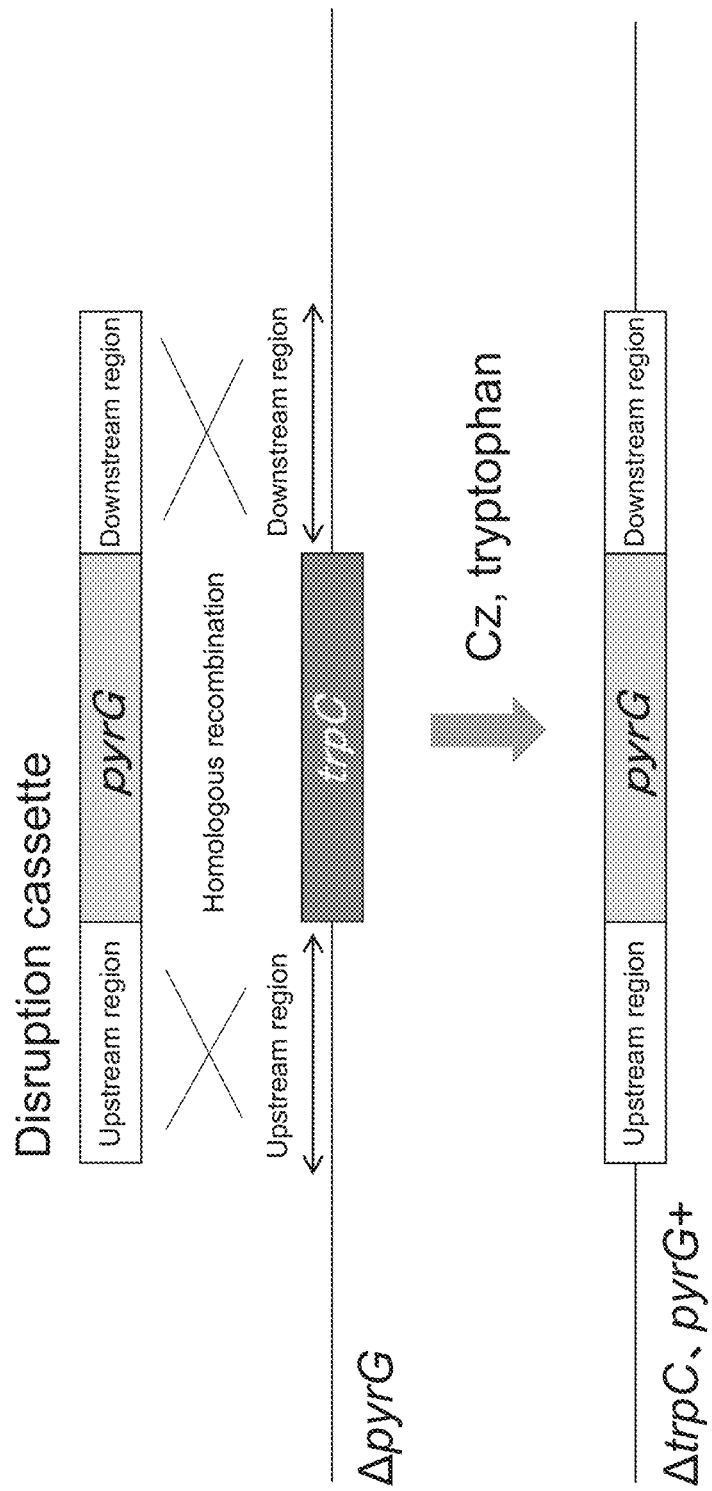
FIG. 2 is a schematic figure of the transformation of *Aspergillus sojae* KP-del strain using the AstrpC disruption cassette, as described in Examples below.

An *Aspergillus sojae* KP-del strain with disruptions of pyrG gene and ku70 gene on chromosomes of *Aspergillus sojae* NBRC4239 strain was prepared as a host organism according to the description of Example 2 in the Japanese Patent No. JP6261039 B. The ku70 gene is a gene involved in non-homologous recombination, and the disruption of ku70 gene is directed to the improved efficiency of gene targeting. An outline of the transformation of *Aspergillus sojae* KP-del strain using the AstrpC disruption cassette is shown in FIG. 2. As shown in FIG. 2, the transformation using the AstrpC disruption cassette resulted in an AstrpC-disrupted strain in which the pyrG gene was introduced into the locus of trpC gene on chromosomes of *Aspergillus sojae* KP-del strain. The AstrpC-disrupted strain lacked the trpC gene and had the pyrG gene.

In a 500 ml Erlenmeyer flask, the conidia of the *Aspergillus sojae* KP-del strain were inoculated into 100 ml of a polypeptone dextrin liquid medium containing 20 mM uracil and 20 mM uridine. The inoculated medium was subjected to shake culture at 30° C. for about 20 hours. After the culture, the cells were collected. Protoplasts were prepared from the collected cells. The resulting protoplasts were then transformed with 20 μg of the AstrpC disruption cassette by PEG-mediated protoplast transformation and the transformants were incubated at 30° C. for days or more in Czapek-Dox minimal medium (Difco; pH 6) containing 1 mM tryptophan, 0.5% (w/v) agar and 1.2 M sorbitol to obtain the transformed *Aspergillus sojae* having the ability to form a colony.

In the transformed *Aspergillus sojae* in which the AstrpC gene was disrupted, the AspyrG gene introduced into the locus of the AstrpC gene allowed the transformant to complement the uracil requirement of the host organism and to require tryptophan instead.

(1-5) Selection of AstrpC-Disrupted Strain

A strain in which the AstrpC gene was disrupted was selected by PCR using the chromosomal DNA of the transformed *Aspergillus sojae* extracted according to (1-2) above to serve as a template DNA. Primers used are the primers of SEQ ID NOs: 9 to 12.

By carrying out PCR described above, a PCR product of 692 bp derived from the AstrpC gene was not confirmed while a PCR product of 439 bp derived from Aslig1 gene, which was not the target of disruption, was confirmed by agarose electrophoresis, and the AstrpC disruption strain was selected.

Using the selected AstrpC-disrupted strain, PCR and restriction enzyme digestion of PCR product were performed to confirm that the AstrpC disruption cassette was introduced by homologous recombination. Primers used are the primers of SEQ ID NOs: 13 to 14.

With the AstrpC-disrupted strain, a PCR product of 5.7 kb was amplified, and then by digesting the PCR product with KpnI, the fragments of 2.4 kb, 2.1 kb, and 1.2 kb were obtained. In addition, with the host strain, a PCR product of 6.4 kb was amplified, and then by digesting the PCR product with KpnI, the fragments of 3.5 kb, and 2.9 kb were obtained.

(1-6) Confirmation of Tryptophan Requirement

The AstrpC-disrupted strain into which the AstrpC disruption cassette was introduced by homologous recombination was inoculated onto the plates of Czapek-Dox minimal agar medium with or without 1 mM tryptophan, and incubated at 30° C. for 4 days. It was confirmed that the strain grew only in the medium with tryptophan.

(1-7) Confirmation of 5-FAA Resistance of AstrpC-Disrupted Strain

The AstrpC-disrupted strain and *Aspergillus sojae* NBRC4239 strain as a control were inoculated onto the plates of potato dextrose agar medium (Nissui Pharmaceutical Co., Ltd.) containing 0.04% (w/v) 5-FAA and 1 mM tryptophan, respectively. The plates were incubated at 30° C. for 4 days. The NBRC4239 strain did not grow at all, whereas the AstrpC-disrupted strain grew. As a result, it was confirmed that the AstrpC-disrupted strain showed a resistance to 5-FAA. In addition, 5-FAA (5-fluoroanthranilic acid; Tokyo Chemical Industry Co., Ltd.) was prepared to become a 10% solution using ethanol, and the solution was added to the medium to ensure that the final concentration became the above-mentioned concentration.

When the concentration of 5-FAA was changed to 0.02% (w/v), both AstrpC-disrupted and NBRC4239 strains grew on the plates. Therefore, it was found that 0.04% (w/v) 5-FAA could be used to select an AstrpC-disrupted strain for *Aspergillus sojae*.

2. Gene Disruption Using AstrpC Marker Gene (2-1) Target Gene for Disruption

The gene to be disrupted was directed to poly(ADP-ribose) polymerase gene predicted to be located in the region 3347080-3344733 of scaffold 00063 (DF093585.1) from the public genome database of *Aspergillus sojae* NBRC4239 (BioProject Accession: PRJDA60265). The gene was referred to as Asparp1 gene.

(2-2) Preparation of Plasmid Containing AstrpC Disruption Cassette

According to the method described in (1-2) above, prepared was a plasmid pPARP1_LO_Trp in which an upstream region 2 for homologous recombination (As upstream region 2), a region 1 for looping out (As loop-out region 1), the AstrpC gene, and a downstream region 2 for homologous recombination (As downstream region 2) were ligated into plasmid pUC19 in sequence. Primers used are the primers of SEQ ID NOs: 15 to 22.

(2-3) Amplification of Asparp1 Disruption Cassette

Using the plasmid pPARP1_LO_Trp obtained in (2-2) above to serve as a template DNA, the Asparp1 disruption cassette was obtained by carrying out PCR and purification of PCR product according to the description in (1-3) above. Primers used are the primers of SEQ ID NOs: 23 to 24.

As such, the Asparp1 disruption cassette was obtained in which the sequences of [As upstream region 2]-[As loop-out region 1]-[AstrpC]-[As downstream region 2] were ligated in sequence.

(2-4) Preparation of Asparp1-Disrupted Strain

Figure 3:
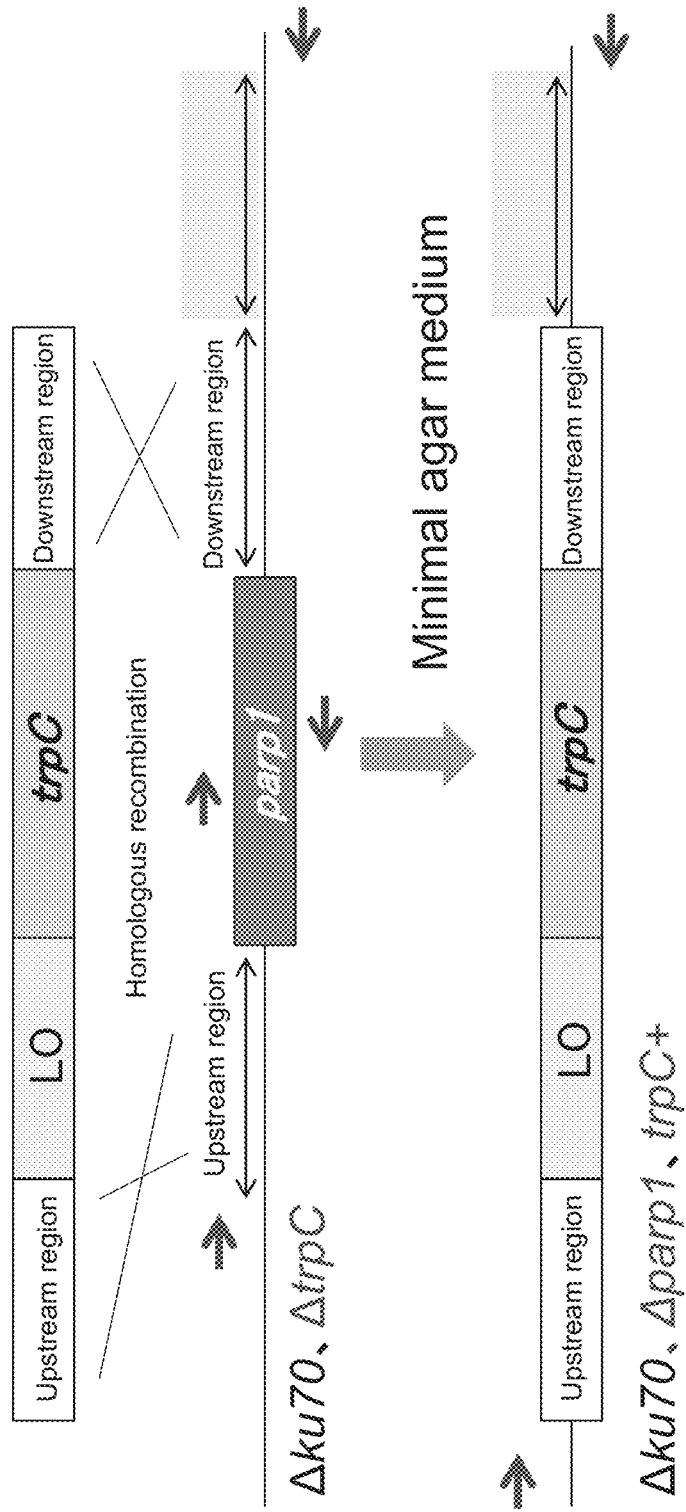
FIG. 3 is a schematic figure of the transformation of the AstrpC-disrupted strain using the Asparp1 disruption cassette, as described in Examples below.

The Asparp1-disrupted strain was prepared by the following procedures. In addition, FIG. 3 represents an outline of transformation of an AstrpC-disrupted strain using the Asparp1 disruption cassette. As shown in FIG. 3, the transformation using the Asparp1 disruption cassette resulted in an AstrpC-disrupted strain in which the trpC gene was introduced into the locus of parp1 gene on chromosomes of the AstrpC-disrupted strain. The AstrpC-disrupted strain lacked the parp1 gene and had the trpC gene.

In a 500 ml Erlenmeyer flask, the conidia of the AstrpC-disrupted strain were inoculated into 100 ml of a polypeptone dextrin liquid medium containing 1 mM tryptophan. The inoculated medium was subjected to shake culture at 30° C. for about 24 hours. After the culture, the cells were collected. Protoplasts were prepared from the collected cells. The resulting protoplasts were then transformed with 20 μg of the Asparp1 disruption cassette by PEG-mediated protoplast transformation and the transformants were incubated at 30° C. for 5 days or more in Czapek-Dox minimal medium containing 0.5% (w/v) agar and 1.2 M sorbitol to obtain the transformed *Aspergillus sojae* having the ability to form a colony.

In the transformed *Aspergillus sojae* in which the Asparp1 gene was disrupted, the AstrpC gene introduced into the locus of the Asparp1 gene allowed the transformant to complement the tryptophan requirement of the host organism.

(2-5) Selection of Asparp1-Disrupted Strain

A strain in which the AstrpC gene was disrupted was selected by PCR using the chromosomal DNA of the transformed strain extracted according to the description in (1-5) above. Primers used are the primers of SEQ ID NOs: 25 to 28.

By carrying out PCR described above, a PCR product of 460 bp derived from the Asparp1 gene was not confirmed while a PCR product of 720 bp derived from AsPtef promoter, which was not the target gene for disruption, was confirmed by agarose electrophoresis. The results of agarose gel electrophoresis are shown in FIG. 4A. As shown in FIG. 4A, no PCR product (PARP) of the parp1 gene was produced using the transformants 2, 6, and 7.

Using the selected Asparp1-disrupted strain, PCR and agarose gel electrophoresis were performed to confirm that the Asparp1 disruption cassette was introduced by homologous recombination. Primers used are the primers of SEQ ID NOs: 29 to 30.

Figure 4B:
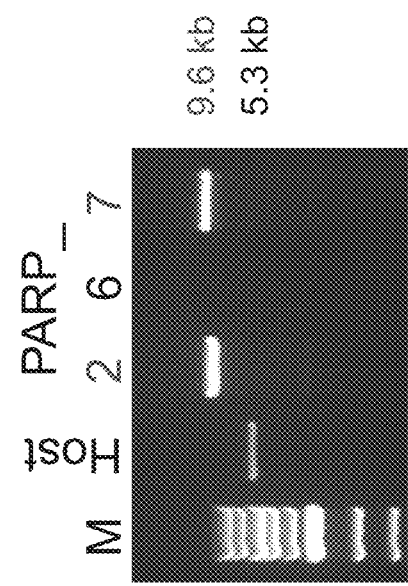
FIG. 4B shows the results of agarose gel electrophoresis for the selection of the Asparp1-disrupted strain, as described in Examples below.

The results of agarose gel electrophoresis are shown in FIG. 4B. As shown in FIG. 4B, a PCR product of 9.6 kb was produced using the transformants 2 and 7 among the transformants 2, 6, and 7. In the host strain, a PCR product of 5.3 kb was produced. As a result, the transformants 2 and 7 (PARP_2 and PARP_7, respectively) were designated as Asparp1-disrupted strains.

3. Removal of AstrpC Marker Gene Introduced (3-1) Confirmation of AstrpC-Deleted Strain As an outline was shown in FIG. 5, the following procedures enabled to select a strain in which the trpC introduced into the Asparp1-disrupted strain was removed by looping out, and thus the trpC and parp1 genes were removed.

Figure 5:
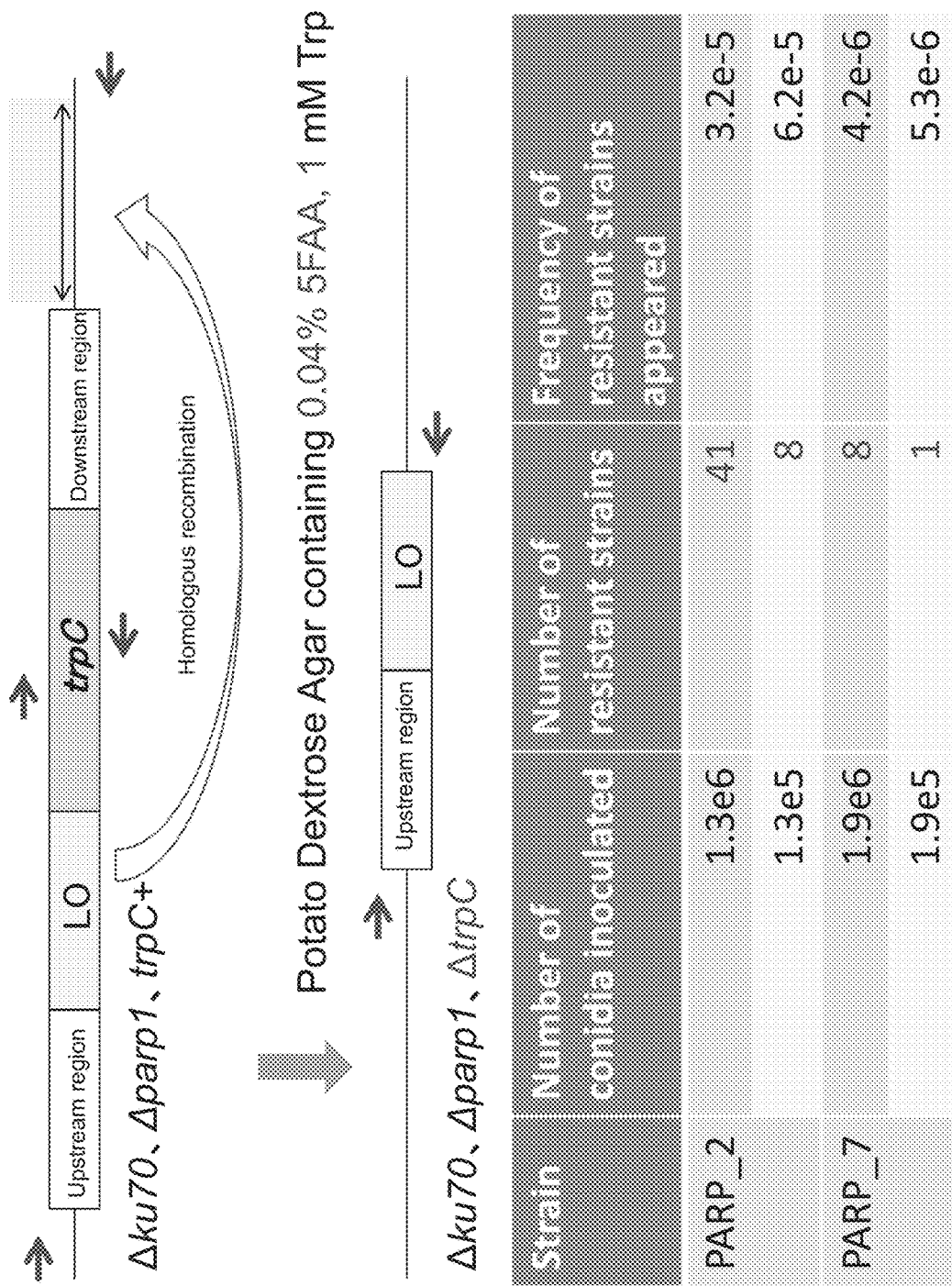
FIG. 5 shows an outline of the selection procedure for the strain in which the trpC and parp1 genes were removed by looping out the trpC gene introduced into the Asparp1-disrupted strain, and the frequency of occurrence of 5-FAA-resistant strains, as described in Examples below.

The conidia of the Asparp1-disrupted strain were inoculated onto the plate of potato dextrose agar medium (Nissui Pharmaceutical Co., Ltd.) containing 0.04% (w/v) 5-FAA and 1 mM tryptophan, and then was incubated at 30° C. for 4 days. FIG. 5 shows the number of conidia of PARP_2 and PARP_7 inoculated, the number of resistant strains appeared, and the frequency of resistant strains appeared calculated from these numbers.

By PCR using the chromosomal DNA extracted from the resulting 5-FAA resistant strain and the primers of SEQ ID NOs: 29 to 30, and agarose gel electrophoresis, it was confirmed that the strain was an AstrpC-deleted strain in which the AstrpC gene was removed by looping out. The results of agarose gel electrophoresis directed to the seven strains showing 5-FAA resistance selected from the PARP 7 strains are shown in FIG. 6A.

Figure 6A:
FIG. 6A shows the results of agarose gel electrophoresis for the selection of the AstrpC-deleted strain, as described in Examples below.

As shown in FIG. 6A, the looping out resulted in a PCR product of 3.0 kb, as expected. If the looping out would not occur, a PCR product of 9.6 kb should have been generated.

Figure 6B:
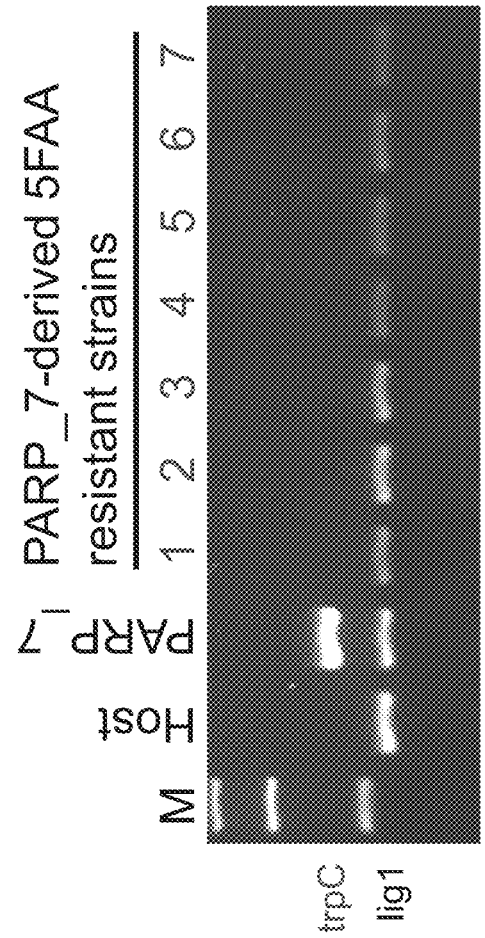
FIG. 6B shows the results of agarose gel electrophoresis for the selection of the AstrpC-deleted strain, as described in Examples below.

By carrying out PCR using the chromosomal DNA extracted from the AstrpC-deleted strain and the primers of SEQ ID NOs: 9 to 12, a PCR product of 692 bp derived from the AstrpC gene was not confirmed while a PCR product of 439 bp derived from Aslig1 gene, which was not the target gene for disruption, was confirmed by agarose electrophoresis. The results of agarose gel electrophoresis directed to the seven strains showing 5-FAA resistance selected from the PARP 7 strains are shown in FIG. 6B. The seven strains were selected as AstrpC-deleted strains.

(3-2) Confirmation of Tryptophan Requirement

The selected AstrpC-deleted strains were inoculated onto the plates of Czapek-Dox minimal agar medium with or without 1 mM tryptophan, and incubated at 30° C. for 4 days. It was confirmed that the AstrpC-deleted strain grew only in the medium with tryptophan, i.e., indicated tryptophan requirement. It was also found that the AstrpC gene could be removed by using 5-FAA.

Example 2: Use of trpC Gene as a Selection Marker Gene Available for Marker Recycling Method in *Aspergillus oryzae*

1. Preparation of AotrpC-Disrupted Strain

In the same manner as in Example 1, DNA fragments of an upstream region 1 for homologous recombination (Ao upstream region 1) and a downstream region 1 for homologous recombination (Ao downstream region 1) were obtained using the chromosomal DNA of *Aspergillus oryzae* RIB40 strain to serve as a template DNA. A plasmid construct pAoTrpC_HR was then prepared by ligating Ao upstream region 1, AspyrG gene, and Ao downstream region 1 in sequence into a plasmid pUC19. Primers used are the primers of SEQ ID NOs: 31 to 34.

The AotrpC disruption cassette was then amplified using the plasmid pAoTrpC_HR to serve as a template DNA in the same manner as in Example 1. Primers used are the primers of SEQ ID NOs: 35 to 36.

As such, the AotrpC disruption cassette was obtained in which the sequences of [Ao upstream region 1]-[AspyrG]-[Ao downstream region 1] were ligated in sequence.

*Aspergillus oryzae* RkuN16ptr1 strain (Mol. Genet. Genomics, 275:460, 2006, Biosci. Biotechnol. Biochem, 70:135, 2006; the entire description is incorporated by reference herein) as described in Japanese Patent No. 5704609 B was used to serve as a host strain for producing an AotrpC-disrupted strain. In addition, in the RkuN16ptr1 strain, the pyrG and ku70 genes have been disrupted.

In a 500 ml Erlenmeyer flask, the conidia of the *Aspergillus oryzae* RkuN16ptr1 strain were inoculated into 100 ml of polypeptone dextrin liquid medium containing 10 mM uracil. The inoculated medium was subjected to shake culture at 30° C. for about 20 hours. After the culture, the cells were collected. Protoplasts were prepared from the collected cells. The resulting protoplasts were then transformed with 20 μg of the AotrpC disruption cassette by PEG-mediated protoplast transformation, and the transformants were incubated at 30° C. for 5 days or more in Czapek-Dox minimal medium containing 1 mM tryptophan, 0.5% (w/v) agar and 1.2 M sorbitol to obtain the transformed *Aspergillus oryzae* having the ability to form a colony.

In the transformed *Aspergillus oryzae* in which the AotrpC gene was disrupted, the AspyrG gene introduced into the locus of the AotrpC gene allowed the transformant to complement the uracil/uridine requirement of the host organism and to require tryptophan instead.

In the same manner as in Example 1, a strain in which the AotrpC gene was disrupted was selected by PCR using the chromosomal DNA of the transformed *Aspergillus oryzae* to serve as a template DNA. Primers used are the primers of SEQ ID NOs: 9 to 10, and 37 to 38.

By carrying out PCR described above, a PCR product of 692 bp derived from the AotrpC gene was not confirmed while a PCR product of 462 bp derived from Aolig1 gene, which was not the target gene for disruption, was confirmed by agarose gel electrophoresis, and the AotrpC-disrupted strain was selected.

Using the selected AotrpC-disrupted strain, PCR and restriction enzyme digestion of PCR products were performed to confirm that the AotrpC disruption cassette was introduced by homologous recombination. Primers used are the primers of SEQ ID NOs: 14 and 39.

With the AotrpC-disrupted strain, a PCR product of 5.7 kb was amplified, and then by digesting the PCR product with KpnI, the fragments of 2.5 kb, 2.1 kb, and 1.2 kb were obtained. In addition, with the host organism, a PCR product of 6.3 kb was amplified, and then by digesting the PCR product with KpnI, the fragments of 3.5 kb, and 2.8 kb were obtained.

The AotrpC-disrupted strain into which the AotrpC disruption cassette was introduced by homologous recombination was inoculated onto the plates of Czapek-Dox minimal agar medium with or without 1 mM tryptophan, and incubated at 30° C. for 5 days. It was confirmed that the AotrpC-disrupted strain could grow only in the medium with tryptophan.

The AotrpC-disrupted strain and *Aspergillus oryzae* RIB40 strain as a control were inoculated onto the plates of Sabouraud Dextrose Agar medium (BD) containing 0.12% (w/v) 5-FAA and 1 mM tryptophan, respectively. The plates were incubated at 30° C. for 4 days. The RIB40 strain did not grow at all, whereas the AotrpC-disrupted strain grew. As a result, it was confirmed that the AotrpC-disrupted strain showed a resistance to 5-FAA.

When the concentration of 5-FAA was changed to 0.1% (w/v), both the AotrpC-disrupted and RIB40 strains grew on the plates. Therefore, it was found that 0.12% (w/v) 5-FAA could be used to select an AotrpC-disrupted strain for *Aspergillus oryzae*.

2. Gene Disruption Using AotrpC Marker Gene

The gene to be disrupted was directed to a gene of uncertain function predicted to be located in the region 1456616-1457378 of SC102 from the public genome database of *Aspergillus oryzae* RIB40 strain (BioProject Accession: PRJNA20809). The gene was referred to as AohypG gene.

In the same manner as in Example 1, DNA fragments of an upstream region 2 for homologous recombination (Ao upstream region 3), AotrpC gene, a region for looping out (Ao loop-out region 1) and a downstream region 2 for homologous recombination (Ao downstream region 2) were obtained using the chromosomal DNA of *Aspergillus oryzae* RIB40 strain to serve as a template DNA.

A plasmid construct pAoHypC_LO_TrpC was then prepared by ligating the Ao upstream region 2, the AotrpC gene, the Ao loop-out region 1, and the Ao downstream region 2 in sequence into plasmid pUC19. Primers used are the primers of SEQ ID NOs: 20, and 40 to 46.

The AohypG disruption cassette was then amplified using the above plasmid pAoHypG_LO_TrpC to serve as a template DNA in the same manner as in Example 1. Primers used are the primers of SEQ ID NOs: 47 to 48.

As such, the AohypG disruption cassette was obtained in which the sequences of [Ao upstream region 2]-[AotrpC]-[Ao loop-out region 1]-[Ao downstream region 2] were ligated in sequence.

Figure 7:
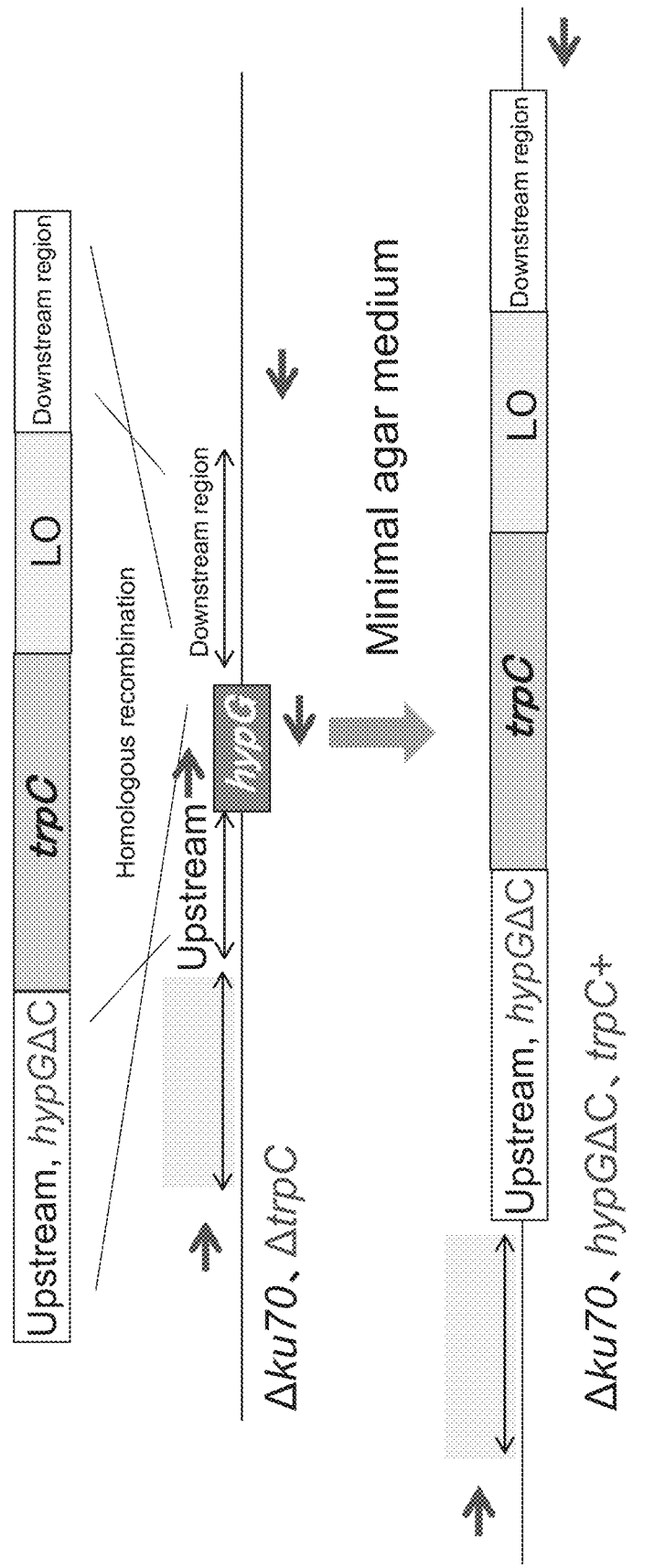
FIG. 7 is a schematic figure of the transformation of the AotrpC-disrupted strain using the AohypG disruption cassette, as described in Examples below.

An AohypG-disrupted strain was prepared by the following procedures. In addition, FIG. 7 represents an outline of transformation of an AotrpC-disrupted strain using the AohypG disruption cassette. As shown in FIG. 7, the transformation using the AohypG disruption cassette resulted in an AotrpC-disrupted strain in which the trpC gene was introduced into the locus of the hypG gene on chromosomes of the AotrpC-disrupted strain. The AotrpC-disrupted strain lacked the hypG gene and had the trpC gene.

In a 500 ml Erlenmeyer flask, the conidia of the *Aspergillus oryzae* AotrpC-disrupted strain were inoculated into 100 ml of a potato dextrose liquid medium (BD) containing 1 mM tryptophan. The inoculated medium was subjected to shake culture at 30° C. for about 24 hours. After the culture, the cells were collected. Protoplasts were prepared from the collected cells. The resulting protoplasts were then transformed with 20 µg of the AohypG disruption cassette by PEG-mediated protoplast transformation and the transformants were incubated at 30° C. for 5 days or more in Czapek-Dox minimal medium containing 0.5% (w/v) agar and 1.2 M sorbitol to obtain the transformed *Aspergillus oryzae* having the ability to form a colony.

In the transformed *Aspergillus oryzae* in which the AohypG gene was disrupted, the AotrpC gene introduced into the locus of the AohypG gene allowed the transformant to complement the tryptophan requirement of the host organism.

A strain in which the AohypG gene was disrupted was selected by PCR using the chromosomal DNA of the transformed strain extracted in the same manner as in Example 1. Primers used are the primers of SEQ ID NOs: 37 to 38, and 49 to 50.

By carrying out PCR described above, a PCR product of 702 bp derived from the AohypG gene was not confirmed while a PCR product of 462 bp derived from Aolig1 gene, which was not the target gene for disruption, was confirmed by agarose gel electrophoresis, and the AohypG-disrupted strain was selected.

Using the selected AohypG-disrupted strain, it was confirmed that the AohypG disruption cassette was introduced by homologous recombination by conducting PCR. Primers used are the primers of SEQ ID NOs: 51 to 52.

In the AohypG-disrupted strain, a PCR product of 8.6 kb was produced. In the host organism, a PCR product of 4.3 kb was produced.

3. Removal of AotrpC Marker Gene Introduced

Figure 8:
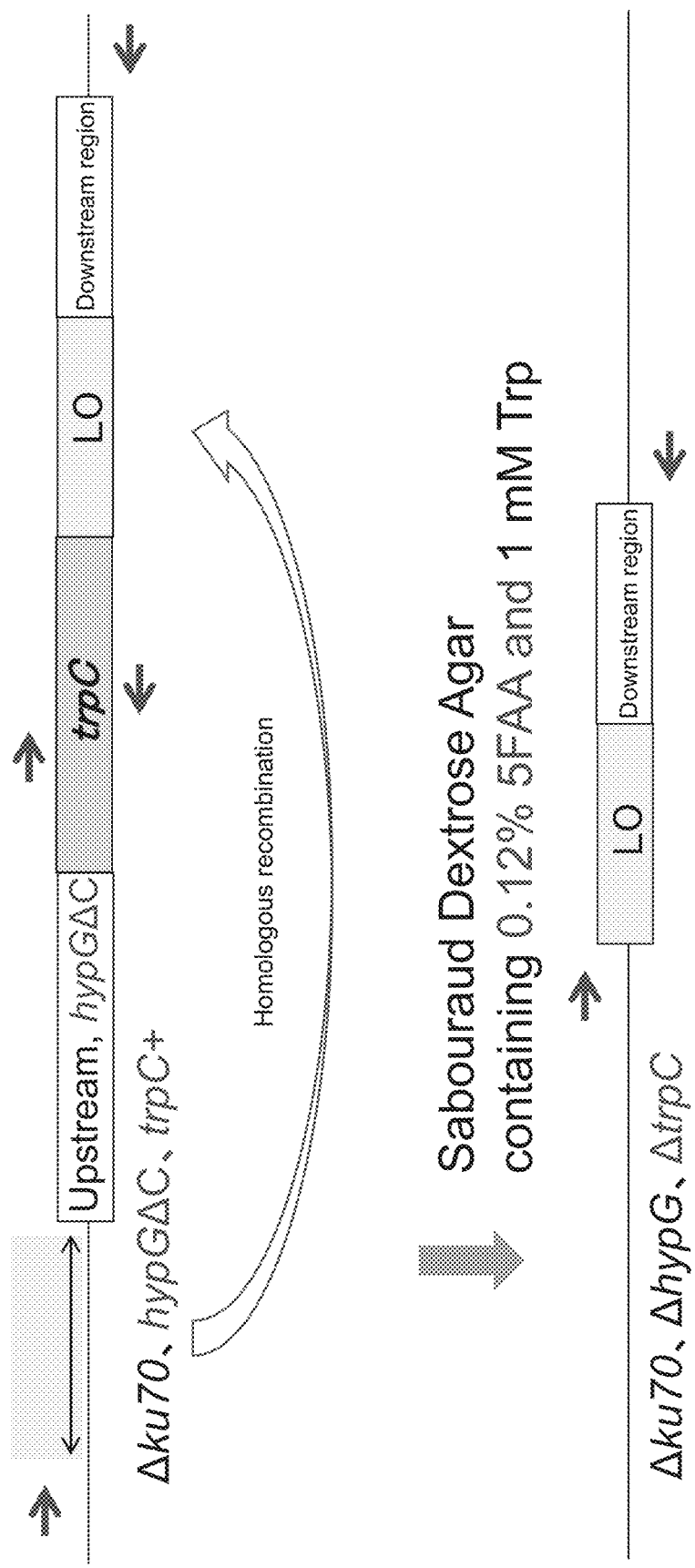
FIG. 8 shows an outline of the selection procedure for the strain in which the trpC and hypG genes were removed by looping out the trpC gene introduced into the AohypG-disrupted strain, as described in Examples below.

As an outline has been shown in FIG. 8, the following procedures enabled to select a strain in which the trpC introduced into the AohypG-disrupted strain was removed by looping out, and thus the trpC and hypG genes were removed.

The conidia of AohypG-disrupted strain were inoculated onto the plate of Sabouraud Dextrose agar medium (BD) containing 0.12% (w/v) 5-FAA and 1 mM tryptophan, and then were incubated at 30° C. for 5 days or more.

By PCR using the chromosomal DNA extracted from the resulting 5-FAA resistant strain and the primers of SEQ ID NOs: 51 to 52, and agarose gel electrophoresis, it was confirmed that the strain was an AotrpC-deleted strain in which the AotrpC gene was removed by looping out. The results of agarose gel electrophoresis directed to the resulting six strains showing 5-FAA resistance are shown in FIG. 9A.

As shown in FIG. 9A, in either 5-FAA resistant strain, the looping out occurred thereby resulting in a PCR product of 2.7 kb, as expected. If the looping out would not occur, a PCR product of 8.6 kb should have been generated.

By carrying out PCR using the chromosomal DNA extracted from the 5-FAA resistant strain and the primers of SEQ ID NOs: 9 to 10, and 37 to 38, a PCR product of 692 bp derived from the AotrpC gene was not confirmed while a PCR product of 462 bp derived from Aolig1 gene, which was not the target gene for disruption, was confirmed by agarose electrophoresis. The results of agarose gel electrophoresis directed to the resulting six strains showing 5-FAA resistance are shown in FIG. 9B. The six strains were selected as AotrpC-deleted strains.

In the same manner as in Example 1, it was confirmed that the AotrpC-deleted strain grew only in the medium containing tryptophan, i.e., showed a tryptophan requirement. It was also found that the AotrpC gene could be removed by using 5-FAA.

Example 3: Use of trpC Gene as a Selection Marker Gene Available for Marker Recycling Method in *Aspergillus niger*

1. Preparation of AntrpC-Disrupted Strain

In the same manner as in Example 1, DNA fragments of an upstream region 1 for homologous recombination (An upstream region 1) and a downstream region 1 for homologous recombination (An downstream region 1) were obtained using the chromosomal DNA of *Aspergillus niger* A1179 strain (AkusA, pyrG-; obtained from Fungal Genetics Stock Center) to serve as a template DNA. A plasmid construct pAnTrpC_HR was then prepared by ligating the An upstream region 1, the AspyrG gene, and the An downstream region 1 in sequence into plasmid pUC19. Primers used are the primers of SEQ ID NOs: 53 to 56.

The AntrpC disruption cassette was then amplified using the plasmid pAnTrpC_HR to serve as a template DNA in the same manner as in Example 1. Primers used are the primers of SEQ ID NOs: 57 to 58.

As such, the AntrpC disruption cassette was obtained in which the sequences of [An upstream region 1]-[AspyrG]-[An downstream region 1] were ligated in sequence.

In a 500 ml Erlenmeyer flask, the conidia of *Aspergillus niger* A1179 strain were inoculated into 100 ml of potato dextrose liquid medium (BD) containing 10 mM uracil and 10 mM uridine. The inoculated medium was subjected to shake culture at 30° C. for about 16 hours. After the culture, the cells were collected. Protoplasts were prepared from the collected cells. The resulting protoplasts were then transformed with 20 µg of AntrpC disruption cassette by PEG-mediated protoplast transformation, and the transformants were then incubated at 30° C. for 4 days or more in Czapek-Dox minimal medium containing 1 mM tryptophan, 0.5% (w/v) agar and 1.2 M sorbitol to obtain the transformed *Aspergillus niger* having the ability to form a colony.

In the transformed *Aspergillus niger* in which the AntrpC gene was disrupted, the AspyrG gene introduced into the locus of the AntrpC gene allowed the transformant to complement the uracil requirement of the host organism and to require tryptophan instead.

In the same manner as in Example 1, a strain in which the AntrpC gene was disrupted was selected by PCR using the chromosomal DNA of the transformed *Aspergillus niger* to serve as a template DNA. Primers used are the primers of SEQ ID NOs: 59 to 62.

By carrying out PCR described above, a PCR product of 420 bp derived from the AntrpC gene was not confirmed while a PCR product of 862 bp derived from the AspyrG gene introduced was confirmed by agarose gel electrophoresis, and the AntrpC-disrupted strain was selected.

Using the selected AntrpC-disrupted strain, it was confirmed that by conducting PCR and restriction enzyme digestion of PCR products, the AntrpC disruption cassette was introduced by homologous recombination. Primers used are the primers of SEQ ID NOs: 63 to 64.

With the AntrpC-disrupted strain, a PCR product of 5.5 kb was amplified, and then by digesting the PCR product with KpnI, the fragments of 2.4 kb, 2.0 kb, and 1.2 kb were obtained. In the host organism, a PCR product of 6.1 kb was produced, but the PCR product was not digested by KpnI.

The AntrpC-disrupted strain into which the AntrpC disruption cassette was introduced by homologous recombination was inoculated onto the plates of Czapek-Dox minimal agar medium with or without 1 mM tryptophan, and incubated at 30° C. for 7 days. It was confirmed that the AntrpC-disrupted strain could grow only in the medium with tryptophan.

2. Gene Disruption Using AntrpC Marker Gene

The gene to be disrupted was directed to a gene encoding TpsC, which is a trehalose 6-phosphate synthase, of *Aspergillus niger* (BMC Microbiol 14, 90 (2014), [Website] https://www.ncbi.nlm.nih.gov/pmc/articles/PMC 3991884/; the entire description is incorporated by reference herein). The gene was referred to as AntpsC gene.

In the same manner as in Example 1, DNA fragments of an upstream region 2 for homologous recombination (An upstream region 2), a region for looping out (An loop-out region 1), AntrpC gene and a downstream region 2 for homologous recombination (An downstream region 2) were obtained using the chromosomal DNA of *Aspergillus niger* A1179 strain to serve as a template DNA. A plasmid construct pAnTpsC_LO_TrpC was then prepared by ligating the An upstream region 2, the An loop-out region 1, the AntrpC gene, and the An downstream region 2 in sequence into plasmid pUC19. Primers used are the primers of SEQ ID NOs: 65 to 72.

The AntpsC disruption cassette was then amplified using the above plasmid pAnTpsC_LO_TrpC to serve as a template DNA in the same manner as in Example 1. Primers used are the primers of SEQ ID NOs: 73 to 74.

As such, the AntpsC disruption cassette was obtained in which the sequences of [An upstream region 2]-[An loop-out region 1]-[AntrpC]-[An downstream region 2] were ligated in sequence.

An AntpsC-disrupted strain was prepared by transforming the AntrpC-disrupted strain with the use of the AntpsC disruption cassette according to the following procedures.

In a 500 ml Erlenmeyer flask, the conidia of the *Aspergillus niger* AntrpC-disrupted strain were inoculated into 100 ml of potato dextrose liquid medium containing 1 mM tryptophan. The inoculated medium was subjected to shake culture at 30° C. for about 16 hours. After the culture, the cells were collected. Protoplasts were prepared from the collected cells. The resulting protoplasts were then transformed with 20 μg of AntpsC disruption cassette by PEG-mediated protoplast transformation, and the transformants were then incubated at 30° C. for 4 days or more in Czapek-Dox minimal medium containing 0.5% (w/v) agar and 1.2 M sorbitol to obtain the transformed *Aspergillus niger* having the ability to form a colony.

In the transformed *Aspergillus niger* in which the AntpsC gene was disrupted, the AntrpC gene introduced into the locus of the AntpsC gene allowed the transformant to complement the tryptophan requirement of the host organism.

A strain in which the AntpsC gene was disrupted was selected by PCR using the chromosomal DNA of the transformed strain extracted in the same manner as in Example 1. Primers used are the primers of SEQ ID NOs: 61 to 62, and 75 to 76.

By carrying out PCR described above, a PCR product of 430 bp derived from the AntpsC gene was not confirmed while a PCR product of 862 bp derived from the AspyrG gene introduced was confirmed by agarose gel electrophoresis, and the AntpsC-disrupted strain was selected.

Using the selected AntpsC-disrupted strain, it was confirmed that by conducting PCR, the AntpsC disruption cassette was introduced by homologous recombination. Primers used are the primers of SEQ ID NOs: 77 to 78.

In the AntpsC-disrupted strain, a PCR product of 9.1 kb was produced. In the host organism, a PCR product of 5.9 kb was produced.

3. Removal of AntrpC Marker Gene Introduced

The conidia of the AntpsC-disrupted strain were inoculated onto the plate of potato dextrose agar medium containing 0.015% (w/v) 5-FAA and 1 mM tryptophan, and the inoculated plate was then incubated at 30° C. for 4 days or more.

By PCR using the chromosomal DNA extracted from the resulting 5-FAA resistant strain and the primers of SEQ ID NOs: 77 to 78, and agarose gel electrophoresis, it was confirmed that the strain was an AntrpC-deleted strain in which the AntrpC gene was removed by looping out.

The looping out resulted in a PCR product of 2.9 kb, as expected. If the looping out would not occur, a PCR product of 9.1 kb should have been generated.

In the same manner as in Example 1, it was confirmed that the AntrpC-deleted strain grew only in the medium containing tryptophan, i.e., showed a tryptophan requirement. It was also found that the AntrpC gene could be removed by using 5-FAA.

Figure 10:
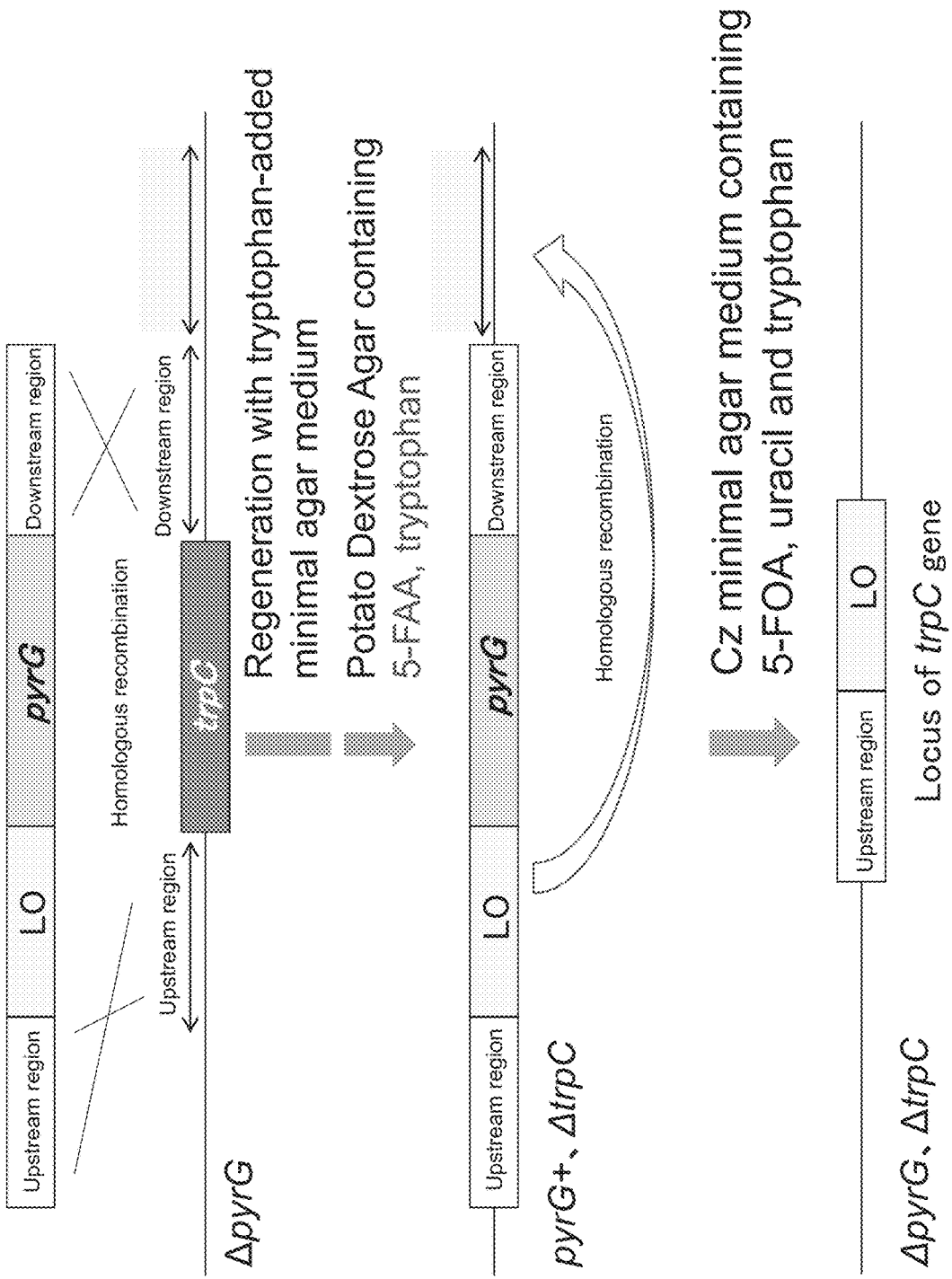
FIG. 10 shows an outline of the production procedure of the AspyrG/AstrpC-double-disrupted strain, as described in Examples below.

Example 4. Preparation of Double-Disrupted Strain Lacking AspyrG and AstrpC Genes An AspyrG/AstrpC-double-disrupted strain was produced by disrupting the AstrpC gene in the AspyrG-disrupted strain of *Aspergillus sojae* with the AspyrG gene followed by removing the introduced AspyrG gene by looping out, according to the following procedures. The preparation procedure of the AspyrG/AstrpC-double-disrupted strain is outlined in FIG. 10.

1. Preparation of AstrpC Disruption Cassette Capable of Looping Out

A vector fragment was obtained by conducting Inverse PCR using the plasmid pTrpC_HR produced in Example 1 to serve as a template DNA followed by purifying the resulting PCR product. Primers used are the primers of SEQ ID NOs: 79 to 80.

A region 2 for looping out (As loop-out region 2) was obtained by conducting PCR using the chromosomal DNA of *Aspergillus sojae* NBRC4239 strain to serve as a template DNA followed by purifying the resulting PCR product. Primers used are the primers of SEQ ID NOs: 81 to 82.

The As loop-out region 2 was ligated into the obtained vector fragment according to the procedure described in (1-2) of Example 1 to obtain a plasmid in which the sequences of [As upstream region 1]-[As loop-out region 2]-[AspyrG]-[As downstream region 1] in sequence were ligated into pUC19 at the multiple cloning site. The resulting plasmid was referred to as pTrpC_LO_pyrG.

The AstrpC disruption cassette capable of looping out was then amplified using the plasmid pTrpC_LO_pyrG to serve as a template DNA in the same manner as in (1-3) of Example 1. Primers used are the primers of SEQ ID NOs: 7 to 8.

As such, the AstrpC disruption cassette capable of looping out was obtained in which the sequences of [As upstream region 1]-[As loop-out region 2]-[AspyrG]-[As downstream region 1] were ligated together in sequence.

2. Preparation of AstrpC-Disrupted Strain

*Aspergillus sojae* KP-del strain was transformed with the AstrpC disruption cassette capable of looping out according to the procedure described in (1-4) of Example 1 to obtain a transformed *Aspergillus sojae*.

In the transformed *Aspergillus sojae* in which the AstrpC gene was disrupted, the AspyrG gene introduced into the locus of the AstrpC gene allowed the transformant to complement the uracil/uridine requirement of the host organism and to require tryptophan instead.

The conidia were collected with the use of 0.01% (w/v) Tween solution from the plates in which the growth of the transformed *Aspergillus sojae* was found. The conidial suspension was prepared by properly diluting the collected conida with the above solution. The conidial suspension was then inoculated onto the plate of potato dextrose agar medium containing 0.04% (w/v) 5-FAA and 1 mM tryptophan, and then was incubated at 30° C. for 4 days.

The resulting 5-FAA resistant strain was inoculated onto the plate of Czapek-Dox minimal agar medium with or without 1 mM tryptophan, and incubated at 30° C. for 4 days. A strain growing only in the medium with tryptophan, i.e., showing a tryptophan requirement was selected.

Using the chromosomal DNA extracted from the strain showing a tryptophan requirement, PCR, restriction enzyme digestion of PCR products, and agarose gel electrophoresis were carried out to confirm that the AstrpC disruption cassette capable of looping out was introduced by homologous recombination. Primers used are the primers of SEQ ID NOs: 13 and 83.

With the AstrpC-disrupted strain, a PCR product of 8.8 kb was amplified, and did not be digested with BamHI. In addition, with the host organism, a PCR product of 8.2 kb was amplified, and then by digesting the PCR product with BamHI, the fragments of 4.3 kb, and 3.8 kb were obtained.

3. Preparation of AspyrG/AstrpC-Double-Disrupted Strain

The conidia of the AntpsC-disrupted strain obtained above were inoculated onto the plate of Czapek-Dox agar medium containing 1 mM tryptophan, 20 mM uracil and 0.3% (w/v) 5-FOA, and the inoculated plate was then incubated at 30° C. for 5 days or more to select a 5-FOA resistant strain. In addition, 5-FOA (5-fluoroorotic acid; Fluorochem) was prepared to be a 1.2% aqueous solution, and the solution was then adjusted at pH 6. The solution was then subjected to filter sterilization and added to the medium in such a way that the final concentration became the above-mentioned concentration.

By PCR using the chromosomal DNA extracted from the resulting 5-FOA resistant strain and the primers of SEQ ID NOs: 13 and 83, it was confirmed that the 5-FOA resistant strain was an AspyrG/AstrpC-double-disrupted strain in which the AspyrG gene was removed from the AstrpC disrupted strain by looping out. In other words, it was confirmed that a PCR product of 3.9 kb was amplified by PCR as expected after looping out. As mentioned above, the PCR product obtained before looping out is 8.8 kb.

4. Confirmation of Tryptophan and Uracil Requirements

The AspyrG/AstrpC-double-disrupted strain was inoculated onto the plate of each agar medium shown in (1) to (4) below and incubated at 30° C. for at least 5 days.

(1) Czapek-Dox minimal agar medium
(2) Czapek-Dox minimal agar medium containing 1 mM tryptophan
(3) Czapek-Dox minimal agar medium containing 20 mM uracil
(4) Czapek-Dox minimal agar medium containing 1 mM tryptophan and 20 mM uracil The AspyrG/AstrpC-double-disrupted strain was grown only in the above medium (4) containing tryptophan and uracil, and was found to be required for both tryptophan and uracil.

5. Confirmation of 5-FOA and 5-FAA Resistances

Using a non-disrupted strain (*Aspergillus sojae* NBRC4239 strain), the AspyrG-disrupted strain (*Aspergillus sojae* Kp-del strain), the AstrpC-disrupted strain (as produced in Example 1), and the AspyrG/AstrpC-double-disrupted strain, it was evaluated whether the strains showed a 5-FOA resistance and a 5-FAA resistance by the following procedure.

The strains were inoculated onto the plate of potato dextrose agar medium containing 1 mM tryptophan, 20 mM uracil, and 5-FOA and 5-FAA at the concentrations as shown in Table 3 and incubated at 30° C. for 4 days. The 5-FOA and 5-FAA resistance of each strain was confirmed by the presence or absence of colony formation on the plate.

TABLE 3

| 5-FOA (%, w/v) | 5-FAA (%, w/v) | Non-disrupted strain | AspyrG-disrupted strain | AstrpC-disrupted strain | AspyrG * AstrpC double-disrupted strain |
|---|---|---|---|---|---|
| 0.3 | 0.04 | − | − | − | − |
| 0.15 | 0.02 | − | − | − | + |
| 0.08 | 0.01 | − | − | − | + |

"+": growth,
"−": no growth

The AspyrG-disrupted strain and the AstrpC-disrupted strain could not grow due to the presence of 5-FAA and 5-FOA in the medium, respectively.

In Example 1, 0.04% (w/v) 5-FAA was used to select the ΔtrpC (AstrpC-disrupted) strain. Furthermore, in Example 4, 0.3% (w/v) 5-FOA was used to select the ΔpyrG (AspyrG-disrupted) strain. However, as shown in Table 3, none of the strains grew in the combination of drugs at the concentrations (0.3% (w/v) 5-FOA and 0.04% (w/v) 5-FAA) when each drug was individually used.

On the other hand, when the concentrations of both drugs were reduced to ½ or further ¼, only the AspyrG/AstrpC-double-disrupted strain grew. Since the effect was observed even when the concentration was reduced to ¼, it was confirmed that 5-FOA and 5-FAA were synergistically effective. It was found that the AspyrG/AstrpC-double-disrupted strain could be selected by using such a medium.

Example 5: Simultaneous Use of pyrG Gene and trpC Gene as Selection Marker Genes Available for Marker Recycling Method 1. Preparation of Asnph disruption cassette The gene to be disrupted was directed to a protease gene predicted to be located in the region 1904082-1905244 of scaffold 00033 (DF093572.1) from the public genome database of *Aspergillus sojae* NBRC4239 (BioProject Accession: PRJDA60265). The gene was referred to as Asnph gene.

According to the procedure described in (1-2) of Example 1 above, prepared was a plasmid pNpH_LO_pyrG in which an upstream region 3 for homologous recombination (As upstream region 3), a region 3 for looping out (As loop-out region 3), AspyrG gene, and a downstream region 3 for homologous recombination (As downstream region 3) were ligated into plasmid pUC19 in sequence. Primers used are the primers of SEQ ID NOs: 84 to 89. The DNA fragment of the AspyrG gene was produced in (1-2) of Example 1.

Using the resulting plasmid pNpH_LO_pyrG to serve as a template DNA, the Asnph disruption cassette was obtained by carrying out PCR and purification of PCR products according to the description in (1-3) above. Primers used are the primers of SEQ ID NOs: 90 to 91.

As such, the Asnph disruption cassette was obtained in which the sequences of [As upstream region 3]-[As loop-out region 3]-[AspyrG]-[As downstream region 3] were ligated together in sequence.

2. Preparation of Asparp1/Asnph-Double Disrupted Strain

Figure 11:
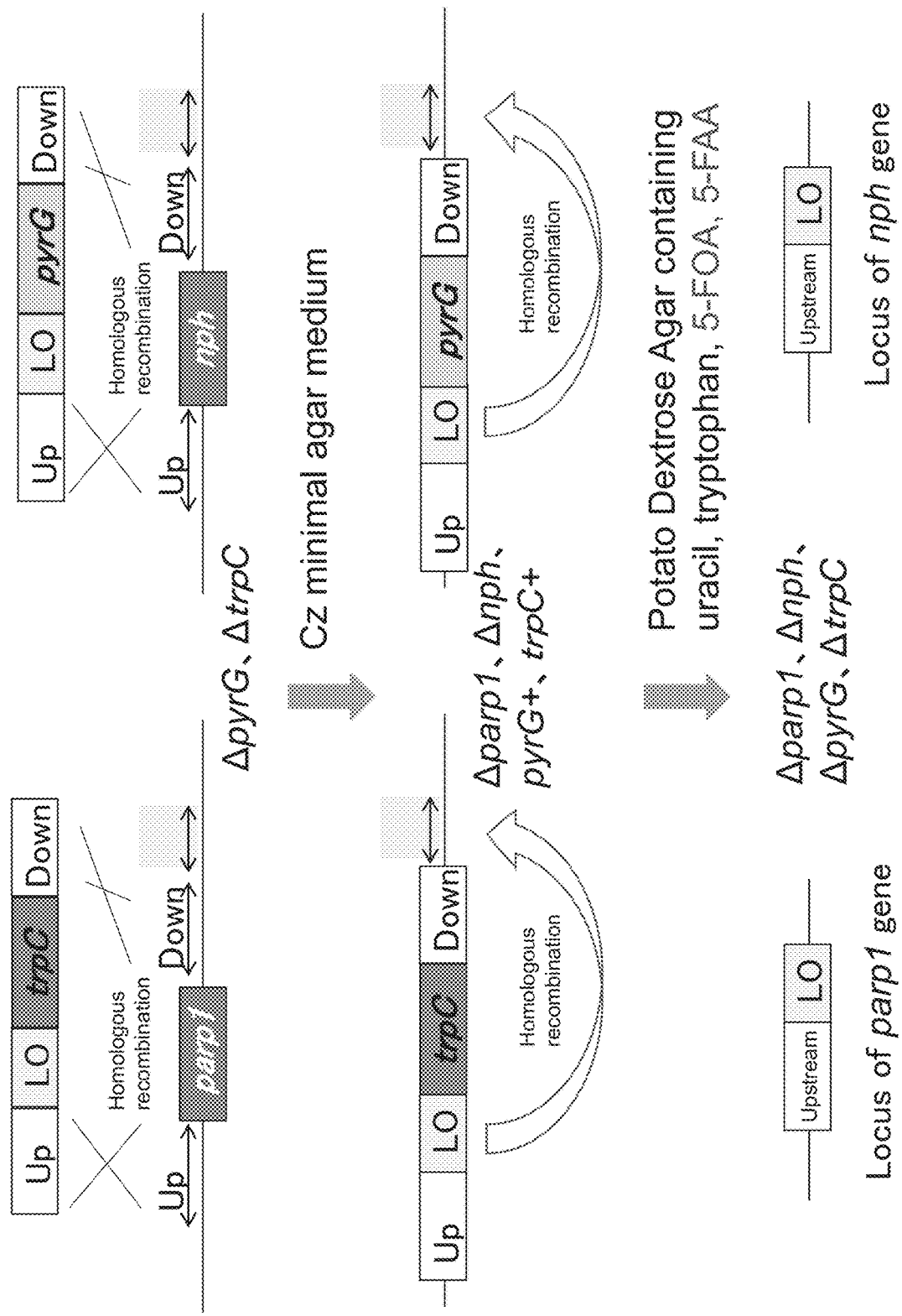
FIG. 11 shows an outline of the production procedure of the Asparp1/Asnph-double-disrupted strain, as described in Examples below.

FIG. 11 shows a schematic overview of the steps of preparing the Asparp1/AstrpC-double-disrupted strain by transforming the AspyrG/AstrpC-double-disrupted strain using the Asparp1 disruption cassette and the Asnph disruption cassette followed by preparing the AspyrG/AstrpC-double-deleted strain by looping out the AspyrG marker gene and the AstrpC marker gene.

In a 500 ml Erlenmeyer flask, the conidia of the *Aspergillus sojae* AspyrG/AstrpC-double-disrupted strain prepared in Example 4 were inoculated into 100 ml of potato dextrose liquid medium containing 1 mM tryptophan, 20 mM uracil and 20 mM uridine. The inoculated medium was subjected to shake culture at 30° C. for about 24 hours. After the culture, the cells were collected. Protoplasts were prepared from the collected cells. The resulting protoplasts were then transformed with 20 μg of Asparp1 disruption cassette (as prepared in Example 1) and 20 μg of Asnph disruption cassette by protoplast PEG-mediated protoplast transformation, and the transformants were incubated at 30° C. for 5 days or more in Czapek-Dox minimal medium containing 0.5% (w/v) agar and 1.2 M sorbitol to obtain the transformed *Aspergillus sojae* having the ability to form a colony.

The uracil and tryptophan requirements of the host organism AspyrG/AstrpC-double-disrupted strain would be complemented by the introduced AspyrG and AstrpC genes, respectively. It is noted that a strain in which either one requirement is complemented could not grow in the above medium.

A strain in which both Asparp1 and Asnph genes were disrupted was selected by PCR using the chromosomal DNA of the transformed strain extracted according to the description in (1-5) above. Primers used are the primers of SEQ ID NOs: 25 to 28, and 92 to 93.

Figure 12:
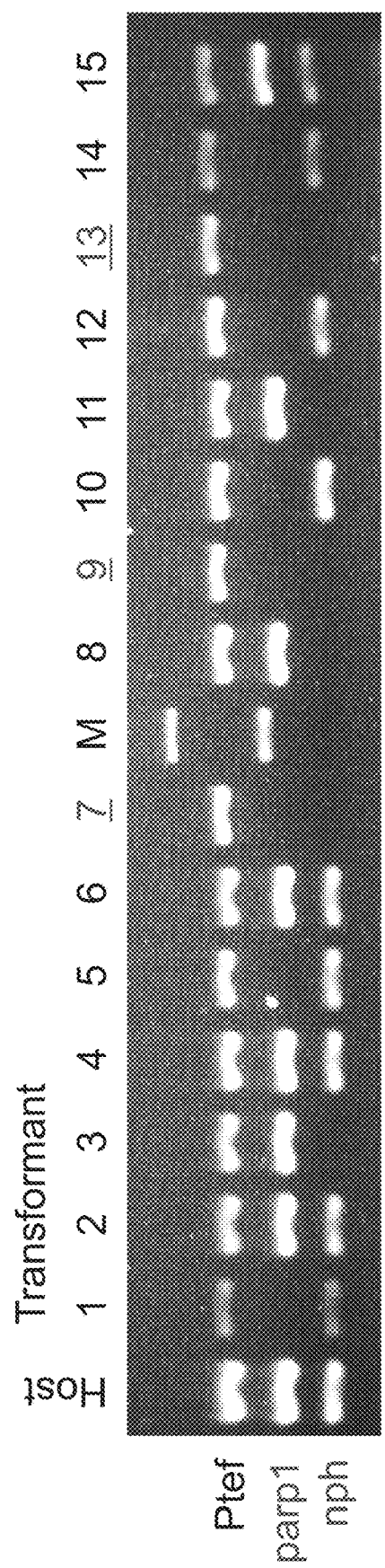
FIG. 12 shows the results of agarose gel electrophoresis for the selection of the Asparp1/Asnph-double-disrupted strain, as described in the examples below.

By carrying out PCR described above, a PCR product of 460 bp derived from the Asparp1 gene and a PCR product of 291 bp derived from the Asnph gene were not confirmed while a PCR product of 720 bp derived from the AsPtef promoter, which was not the target gene for disruption, was confirmed by agarose gel electrophoresis. The results of agarose gel electrophoresis are shown in FIG. 12. The transformed strains 7, 9 and 13 shown in FIG. 12 were selected as the Asparp1/Asnph-double-disrupted strains.

Using the selected Asparp1/Asnph-double-disrupted strain, it was confirmed that by carrying out PCR, the Asparp1 disruption cassette and the Asnph disruption cassette were introduced by homologous recombination. Primers used are the primers of SEQ ID NOs: 29 to 30, and 94 to 95.

The disruption of Asparp1 gene resulted in a PCR product of 9.6 kb. In the host organism, a PCR product of 5.3 kb was produced. The disruption of Asnph gene resulted in a PCR product of 8.5 kb. In the host organism, a PCR product of 5.9 kb was produced.

3. Removal of AspyrG and AstrpC Marker Genes Introduced (3-1) Simultaneously Looping Out The conidia of the Asparp1/Asnph-double-disrupted strain were inoculated onto the plate of potato dextrose agar medium containing 1 mM tryptophan, 20 mM uracil, 0.08% (w/v) 5-FOA and 0.01% (w/v) 5-FAA, and the inoculated plate was then incubated at 30° C. for 10 days or more.

The resulting 5-FOA-resistant and 5-FAA-resistant strain was inoculated onto the above agar plate, and incubated at 30° C. for 4 days to confirm its growth.

By carrying out PCR using the chromosomal DNA extracted from the growing strain and the primers of SEQ ID NOs: 29 to 30, 94 to 95, 9 to 10, 11 to 12 and 61 to 62, and agarose gel electrophoresis, it was confirmed that the strain was an strain in which the AspyrG and AstrpC marker genes were removed. The results of agarose gel electrophoresis directed to the three strains obtained after subjecting the transformed strain 13, which was selected as the Asparp1/Asnph-double-disrupted strain in 2 above, to looping out are shown in FIGS. 13A and 13B.

As shown in FIG. 13A, the looping out occurred around the original locus of Asparp1 gene, and resulted in a PCR product of 3.0 kb, as expected. If the looping out would not occur, a PCR product of 9.6 kb should have been generated.

Figure 13B:
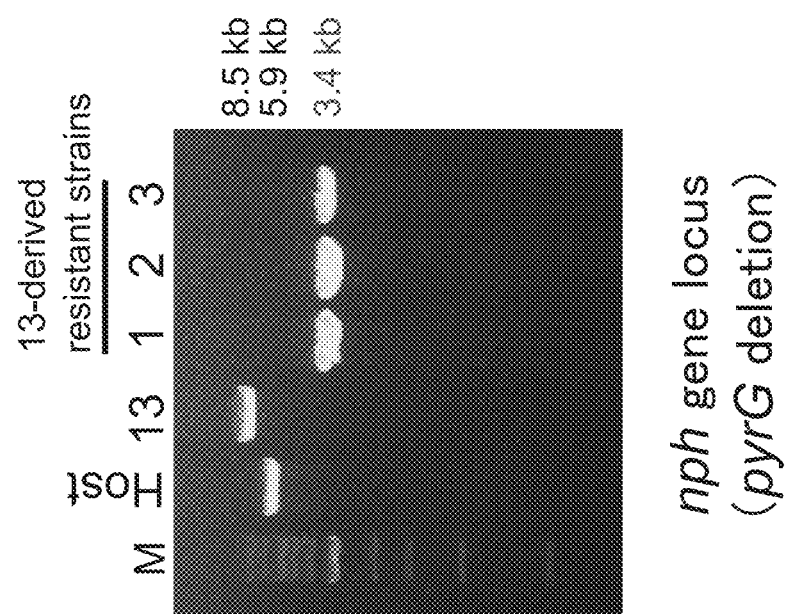
FIG. 13B shows the results of agarose gel electrophoresis for the selection of the AspyrG/AstrpC-double-deleted strain, as described in Examples below.

As shown in FIG. 13B, the looping out occurred around the original locus of Asnph gene, and resulted in a PCR product of 3.4 kb, as expected. If the looping out would not occur, a PCR product of 8.5 kb should have been generated.

By carrying out PCR described above, a PCR product of 862 bp derived from the AspyrG gene and a PCR product of 692 bp derived from the AstrpC gene were not confirmed while a PCR product of 439 bp derived from Aslig1 gene, which was not the target gene for disruption, was confirmed by agarose gel electrophoresis. The results are shown in FIG. 13C. From the above results, the three strains obtained after looping out the transformed strain 13 were selected as AspyrG/AstrpC-double-deleted strains.

The AspyrG/AstrpC-double-deleted strain was inoculated onto the plate of each agar medium shown in (1) to (4) below and incubated at 30° C. for at least 5 days.

(1) Czapek-Dox minimal agar medium
(2) Czapek-Dox minimal agar medium containing 1 mM tryptophan
(3) Czapek-Dox minimal agar medium containing 20 mM uracil
(4) Czapek-Dox minimal agar medium containing 1 mM tryptophan and 20 mM uracil The AspyrG/AstrpC-double-deleted strain grew only in the above medium (4) containing tryptophan and uracil, and was found to be required for both tryptophan and uracil. It was confirmed that the simultaneously looping out of the two marker genes occurred.

(3-2) Two-Step Looping Out

The conidia of the Asparp1/Asnph-double-disrupted strain were inoculated onto the plate of Czapek-Dox agar medium containing 20 mM uracil and 0.3% (w/v) 5-FOA, and the inoculated plate was then incubated at 30° C. for 5 days or more. From the plate onto which a 5-FOA-resistant strain (AspyrG-disrupted strain) grew, the conidia were collected using 0.01% (w/v) Tween 80 solution and properly diluted with the solution to prepare a conidial suspension.

The proper amount of the conidial suspension was inoculated onto the plate of potato dextrose agar medium containing 1 mM tryptophan, 20 mM uracil, 0.08% (w/v) 5-FOA and 0.01% (w/v) 5-FAA, and the inoculated plate was then incubated at 30° C. for 4 days.

The resulting 5-FOA-resistant and 5-FAA-resistant strain was inoculated onto the above agar plate, and incubated at 30° C. for 4 days to confirm its growth.

By carrying out PCR using the chromosomal DNA extracted from the growing strain by the procedure described in (3-1) of Example 5 above, it was confirmed that the strain was an AspyrG/AstrpC-double-deleted strain in which the AspyrG and AstrpC marker genes were removed.

By the procedure described in (3-1) of Example 5 above, it was confirmed that the AspyrG/AstrpC-double-deleted strain showed both tryptophan requirement and uracil requirement. Thus, it was confirmed that the two-step looping out of the two marker genes occurred.

INDUSTRIAL APPLICABILITY

By applying the transformed *Aspergillus* microorganism, composition or method according to one embodiment of the present invention, it is expected to efficiently transform an *Aspergillus* microorganism, which is highly beneficial in the food industry, and further to rapidly detect new phenotypes caused by the simultaneous disruption of genes with similar or related structures or functions harbored in the *Aspergillus* microorganism.

CROSS-REFERENCE TO RELATED APPLICATIONS

This application claims priority to Japanese Patent Application No. 2018-208022 filed on Nov. 5, 2018 and Japanese Patent Application No. 2019-109602 filed on Jun. 12, 2019, which are incorporated herein by reference in their entirety.

SEQUENCE LISTING

19DF0944PCT ST25.txt

The invention claimed is:

1. A transformed *Aspergillus* microorganism totally lacking at least two types of selection marker genes available for marker recycling method on its chromosomes, wherein the selection marker genes comprise trpC gene and pyrG gene; and the transformed *Aspergillus* microorganism is a transformed microorganism of the genus *Aspergillus* different from *Aspergillus aculeatus*.

2. A composition for transforming an *Aspergillus* microorganism different from *Aspergillus aculeatus* according to claim 1, the composition comprising at least two types of nucleic acid fragments comprising a loop-out region and a selection marker gene available for marker recycling method between homologous recombination regions, wherein the nucleic acid fragments comprise a nucleic acid fragment in which the selection marker gene is trpC gene and a nucleic acid fragment in which the selection marker gene is pyrG gene.

3. The transformed *Aspergillus* microorganism according to claim 1, wherein the transformed *Aspergillus* microorganism is a transformed microorganism of *Aspergillus sojae, Aspergillus oryzae, Aspergillus tamarii, Aspergillus luchuensis, Aspergillus usamii* or *Aspergillus saitoi*.

4. A method of producing a transformed *Aspergillus* microorganism totally lacking first and second selection marker genes available for marker recycling method on its chromosomes, the method comprises the steps of:
   (1) subjecting a transformed *Aspergillus* microorganism totally lacking the first selection marker gene on its chromosomes to homologous recombination which targets the second selection marker gene on its chromosomes with the use of a nucleic acid fragment comprising a loop-out region and the first selection marker gene between homologous recombination regions, thereby obtaining a transformed *Aspergillus* microorganism;
   (2) culturing the transformed *Aspergillus* microorganism obtained in the step (1) in the presence of a nutritional substance corresponding to the second selection marker gene to select a transformed *Aspergillus* microorganism inserting the first selection marker gene on its chromosomes and totally lacking the second selection marker gene on its chromosomes; and
   (3) culturing the transformed *Aspergillus* microorganism selected in the step (2) in the presence of a nutritional substance corresponding to the first selection marker gene and an analogue of the nutritional substance as well as a nutritional substance corresponding to the second selection marker gene to select a transformed *Aspergillus* microorganism totally lacking the first and second selection marker genes on its chromosomes;
   wherein one of the first and second selection marker genes is trpC gene and the other is pyrG gene, the nutritional substance corresponding to trpC gene is tryptophan, the analogue of tryptophan is 5-FAA, the nutritional substance corresponding to pyrG gene is uracil and/or uridine, the analogue of uracil and/or uridine is 5-FOA, and the transformed *Aspergillus* microorganism is a transformed microorganism of the genus *Aspergillus* different from *Aspergillus aculeatus*.

5. The method according to claim 4, wherein the transformed *Aspergillus* microorganism is a transformed microorganism of *Aspergillus sojae, Aspergillus oryzae, Aspergillus tamarii, Aspergillus luchuensis, Aspergillus usamii* or *Aspergillus saitoi*.

6. A method of producing a transformed *Aspergillus* microorganism lacking first and second target genes on its chromosomes with the use of first and second selection marker genes available for marker recycling method, the method comprises the steps of:
   (A) subjecting a transformed *Aspergillus* microorganism totally lacking the first and second selection marker genes on its chromosomes to homologous recombination which targets the first and second target genes on its chromosomes with the use of a first nucleic acid fragment comprising a loop-out region and the first selection marker gene between homologous recombination regions for the first target gene and a second nucleic acid fragment comprising a loop-out region and the second selection marker gene between homologous recombination regions for the second target gene, thereby obtaining a transformed *Aspergillus* microorganism; and
   (B) culturing the transformed *Aspergillus* microorganism obtained in the step (A) in the absence of nutritional substances corresponding to the first and second selection marker genes to select a transformed *Aspergillus* microorganism inserting the first and second selection marker genes on its chromosomes;
   wherein one of the first and second selection marker genes is trpC gene and the other is pyrG gene, the nutritional substance corresponding to trpC gene is tryptophan, the analogue of tryptophan is 5-FAA, the nutritional substance corresponding to pyrG gene is uracil and/or uridine, the analogue of uracil and/or uridine is 5-FOA, and the transformed *Aspergillus* microorganism is a transformed microorganism of the genus *Aspergillus* different from *Aspergillus aculeatus*.

7. The method according to claim 6, further comprising the step of:
   (C) culturing the transformed *Aspergillus* microorganism selected in the step (B) in the presence of a nutritional substance corresponding to the first selection marker gene and an analogue of the nutritional substance as well as a nutritional substance corresponding to the second selection marker gene and an analogue of the nutritional substance to select a transformed *Aspergillus* microorganism totally lacking the first and second selection marker genes and the first and second target genes on its chromosomes.

8. The method according to claim 7, wherein the concentration of 5-FAA is in the range between 0.005% (w/v) and 0.02% (w/v); and the concentration of 5-FOA is in the range between 0.05% (w/v) and 0.15% (w/v).

9. The method according to claim 6, wherein the transformed *Aspergillus* microorganism is a transformed microorganism of *Aspergillus sojae, Aspergillus oryzae, Aspergillus tamarii, Aspergillus luchuensis, Aspergillus usamii* or *Aspergillus saitoi*.

* * * * *

```
SEQUENCE LISTING

<160> NUMBER OF SEQ ID NOS: 95

<210> SEQ ID NO 1
<211> LENGTH: 39
<212> TYPE: DNA
<213> ORGANISM: Artificial sequence
<220> FEATURE:
<223> OTHER INFORMATION: Primer

<400> SEQUENCE: 1
cggtacccgg ggatcatgtg gagccaactt tggtagcga                              39

<210> SEQ ID NO 2
<211> LENGTH: 37
<212> TYPE: DNA
<213> ORGANISM: Artificial sequence
<220> FEATURE:
<223> OTHER INFORMATION: Primer

<400> SEQUENCE: 2
tagcaataag cccaatgcgt gagaatcgta agcgcag                                37

<210> SEQ ID NO 3
<211> LENGTH: 28
<212> TYPE: DNA
<213> ORGANISM: Artificial sequence
<220> FEATURE:
<223> OTHER INFORMATION: Primer

<400> SEQUENCE: 3
ttgggcttat tgctatgtcc ctgaaagg                                          28

<210> SEQ ID NO 4
<211> LENGTH: 24
<212> TYPE: DNA
<213> ORGANISM: Artificial sequence
<220> FEATURE:
<223> OTHER INFORMATION: Primer

<400> SEQUENCE: 4
ccgcacctca gaagaaaagg atga                                              24
```

<210> SEQ ID NO 5
<211> LENGTH: 39
<212> TYPE: DNA
<213> ORGANISM: Artificial sequence
<220> FEATURE:
<223> OTHER INFORMATION: Primer

<400> SEQUENCE: 5
tcttctgagg tgcggtctac acctcaattt cgggctgca                          39

<210> SEQ ID NO 6
<211> LENGTH: 37
<212> TYPE: DNA
<213> ORGANISM: Artificial sequence
<220> FEATURE:
<223> OTHER INFORMATION: Primer

<400> SEQUENCE: 6
cgactctaga ggatcaaaaa ctcgacgaag ctgctgc                            37

<210> SEQ ID NO 7
<211> LENGTH: 24
<212> TYPE: DNA
<213> ORGANISM: Artificial sequence
<220> FEATURE:
<223> OTHER INFORMATION: Primer

<400> SEQUENCE: 7
atgtggagcc aactttggta gcga                                          24

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
aaaaactcga cgaagctgct gc                                            22

<210> SEQ ID NO 9
<211> LENGTH: 26
<212> TYPE: DNA
<213> ORGANISM: Artificial sequence
<220> FEATURE:
<223> OTHER INFORMATION: Primer

<400> SEQUENCE: 9
ggacgaattg atcgccaaga agccga                                        26

<210> SEQ ID NO 10
<211> LENGTH: 25
<212> TYPE: DNA
<213> ORGANISM: Artificial sequence
<220> FEATURE:
<223> OTHER INFORMATION: Primer

<400> SEQUENCE: 10
tgttgaggtc gtaagcagcc tgaag                                         25

<210> SEQ ID NO 11
<211> LENGTH: 24
<212> TYPE: DNA
<213> ORGANISM: Artificial sequence
<220> FEATURE:

```
<223> OTHER INFORMATION: Primer

<400> SEQUENCE: 11
atcagctgtc gtgcttgtgt ccca                                              24

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
ccaaccccat tagaagcctg tccatc                                            26

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
atgagatcca ggagcaccgt tcga                                              24

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
ttggcgctta aggtgttgga agg                                               23

<210> SEQ ID NO 15
<211> LENGTH: 39
<212> TYPE: DNA
<213> ORGANISM: Artificial sequence
<220> FEATURE:
<223> OTHER INFORMATION: Primer

<400> SEQUENCE: 15
cggtacccgg ggatctctaa tgcaaacatt gcggctgag                              39

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
tgaatccagt gatggacaat gcga                                              24

<210> SEQ ID NO 17
<211> LENGTH: 38
<212> TYPE: DNA
<213> ORGANISM: Artificial sequence
<220> FEATURE:
<223> OTHER INFORMATION: Primer

<400> SEQUENCE: 17
ccatcactgg attcatgaga taattgctgg gcggtcct                               38
```

```
<210> SEQ ID NO 18
<211> LENGTH: 39
<212> TYPE: DNA
<213> ORGANISM: Artificial sequence
<220> FEATURE:
<223> OTHER INFORMATION: Primer

<400> SEQUENCE: 18
aaagctgtat cttccttaag gcatatcgct ccgcgacct                    39

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
ggaagataca gctttatgc gcaggt                                   26

<210> SEQ ID NO 20
<211> LENGTH: 24
<212> TYPE: DNA
<213> ORGANISM: Artificial sequence
<220> FEATURE:
<223> OTHER INFORMATION: Primer

<400> SEQUENCE: 20
ccgttttggt gtccgattac ggga                                    24

<210> SEQ ID NO 21
<211> LENGTH: 39
<212> TYPE: DNA
<213> ORGANISM: Artificial sequence
<220> FEATURE:
<223> OTHER INFORMATION: Primer

<400> SEQUENCE: 21
cggacaccaa aacggtgtga ctacccagag agaggtgga                    39

<210> SEQ ID NO 22
<211> LENGTH: 39
<212> TYPE: DNA
<213> ORGANISM: Artificial sequence
<220> FEATURE:
<223> OTHER INFORMATION: Primer

<400> SEQUENCE: 22
cgactctaga ggatcttctg gcggatctga gcaacatcg                    39

<210> SEQ ID NO 23
<211> LENGTH: 24
<212> TYPE: DNA
<213> ORGANISM: Artificial sequence
<220> FEATURE:
<223> OTHER INFORMATION: Primer

<400> SEQUENCE: 23
tctaatgcaa acattgcggc tgag                                    24

<210> SEQ ID NO 24
<211> LENGTH: 24
<212> TYPE: DNA
<213> ORGANISM: Artificial sequence
<220> FEATURE:
<223> OTHER INFORMATION: Primer
```

<400> SEQUENCE: 24
ttctggcgga tctgagcaac atcg                                     24

<210> SEQ ID NO 25
<211> LENGTH: 24
<212> TYPE: DNA
<213> ORGANISM: Artificial sequence
<220> FEATURE:
<223> OTHER INFORMATION: Primer

<400> SEQUENCE: 25
gctattttgg ggttgcagcg gatg                                     24

<210> SEQ ID NO 26
<211> LENGTH: 23
<212> TYPE: DNA
<213> ORGANISM: Artificial sequence
<220> FEATURE:
<223> OTHER INFORMATION: Primer

<400> SEQUENCE: 26
tggaactctc ctcgctgaca tca                                      23

<210> SEQ ID NO 27
<211> LENGTH: 23
<212> TYPE: DNA
<213> ORGANISM: Artificial sequence
<220> FEATURE:
<223> OTHER INFORMATION: Primer

<400> SEQUENCE: 27
ccacaactgc ttgggttttg acc                                      23

<210> SEQ ID NO 28
<211> LENGTH: 22
<212> TYPE: DNA
<213> ORGANISM: Artificial sequence
<220> FEATURE:
<223> OTHER INFORMATION: Primer

<400> SEQUENCE: 28
tttgaaggtg gtgcgaactt tg                                       22

<210> SEQ ID NO 29
<211> LENGTH: 25
<212> TYPE: DNA
<213> ORGANISM: Artificial sequence
<220> FEATURE:
<223> OTHER INFORMATION: Primer

<400> SEQUENCE: 29
tccgcaatgg atttaggttg gttcg                                    25

<210> SEQ ID NO 30
<211> LENGTH: 26
<212> TYPE: DNA
<213> ORGANISM: Artificial sequence
<220> FEATURE:
<223> OTHER INFORMATION: Primer

<400> SEQUENCE: 30
gtcgacattc atactgcgcc ttctca                                   26

<210> SEQ ID NO 31
<211> LENGTH: 39

```
<212> TYPE: DNA
<213> ORGANISM: Artificial sequence
<220> FEATURE:
<223> OTHER INFORMATION: Primer

<400> SEQUENCE: 31
cggtacccgg ggatcatgta gagccaactt tggtagcga                                  39

<210> SEQ ID NO 32
<211> LENGTH: 40
<212> TYPE: DNA
<213> ORGANISM: Artificial sequence
<220> FEATURE:
<223> OTHER INFORMATION: Primer

<400> SEQUENCE: 32
tagcaataag cccaactatc gactaagcag cgaccctaac                                 40

<210> SEQ ID NO 33
<211> LENGTH: 40
<212> TYPE: DNA
<213> ORGANISM: Artificial sequence
<220> FEATURE:
<223> OTHER INFORMATION: Primer

<400> SEQUENCE: 33
tcttctgagg tgcggcaact tgtcacagat ccggacgatg                                 40

<210> SEQ ID NO 34
<211> LENGTH: 40
<212> TYPE: DNA
<213> ORGANISM: Artificial sequence
<220> FEATURE:
<223> OTHER INFORMATION: Primer

<400> SEQUENCE: 34
cgactctaga ggatcactcg actgaagctg ctacttccag                                 40

<210> SEQ ID NO 35
<211> LENGTH: 24
<212> TYPE: DNA
<213> ORGANISM: Artificial sequence
<220> FEATURE:
<223> OTHER INFORMATION: Primer

<400> SEQUENCE: 35
atgtagagcc aactttggta gcga                                                  24

<210> SEQ ID NO 36
<211> LENGTH: 25
<212> TYPE: DNA
<213> ORGANISM: Artificial sequence
<220> FEATURE:
<223> OTHER INFORMATION: Primer

<400> SEQUENCE: 36
actcgactga agctgctact tccag                                                 25

<210> SEQ ID NO 37
<211> LENGTH: 23
<212> TYPE: DNA
<213> ORGANISM: Artificial sequence
<220> FEATURE:
<223> OTHER INFORMATION: Primer
```

```
<400> SEQUENCE: 37
gcgaaatcag cgacaccaca cga                                          23

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38
tgtagcctgc accttttcca tggtc                                        25

<210> SEQ ID NO 39
<211> LENGTH: 24
<212> TYPE: DNA
<213> ORGANISM: Artificial sequence
<220> FEATURE:
<223> OTHER INFORMATION: Primer

<400> SEQUENCE: 39
atgagatcca gaagcaccgt tcga                                         24

<210> SEQ ID NO 40
<211> LENGTH: 39
<212> TYPE: DNA
<213> ORGANISM: Artificial sequence
<220> FEATURE:
<223> OTHER INFORMATION: Primer

<400> SEQUENCE: 40
cggtacccgg ggatcgttga tgacggcagg ttttccgtt                         39

<210> SEQ ID NO 41
<211> LENGTH: 40
<212> TYPE: DNA
<213> ORGANISM: Artificial sequence
<220> FEATURE:
<223> OTHER INFORMATION: Primer

<400> SEQUENCE: 41
aaagctgtat ctttccttga agccaaccca ggagacgaag                        40

<210> SEQ ID NO 42
<211> LENGTH: 26
<212> TYPE: DNA
<213> ORGANISM: Artificial sequence
<220> FEATURE:
<223> OTHER INFORMATION: Primer

<400> SEQUENCE: 42
gaaagataca gcttttatgc gcaggt                                       26

<210> SEQ ID NO 43
<211> LENGTH: 39
<212> TYPE: DNA
<213> ORGANISM: Artificial sequence
<220> FEATURE:
<223> OTHER INFORMATION: Primer

<400> SEQUENCE: 43
cggacaccaa aacggcgaag ccgtgcagcc tatagttcc                         39

<210> SEQ ID NO 44
```

-continued

```
<211> LENGTH: 40
<212> TYPE: DNA
<213> ORGANISM: Artificial sequence
<220> FEATURE:
<223> OTHER INFORMATION: Primer

<400> SEQUENCE: 44
tacgtcgatt acccctgtac aggacatgga aaccgctgaa                    40

<210> SEQ ID NO 45
<211> LENGTH: 25
<212> TYPE: DNA
<213> ORGANISM: Artificial sequence
<220> FEATURE:
<223> OTHER INFORMATION: Primer

<400> SEQUENCE: 45
ggggtaatcg acgtacagga cttgg                                    25

<210> SEQ ID NO 46
<211> LENGTH: 39
<212> TYPE: DNA
<213> ORGANISM: Artificial sequence
<220> FEATURE:
<223> OTHER INFORMATION: Primer

<400> SEQUENCE: 46
cgactctaga ggatcaaccc ggcccatttc tacgaagag                     39

<210> SEQ ID NO 47
<211> LENGTH: 24
<212> TYPE: DNA
<213> ORGANISM: Artificial sequence
<220> FEATURE:
<223> OTHER INFORMATION: Primer

<400> SEQUENCE: 47
gttgatgacg gcaggttttc cgtt                                     24

<210> SEQ ID NO 48
<211> LENGTH: 24
<212> TYPE: DNA
<213> ORGANISM: Artificial sequence
<220> FEATURE:
<223> OTHER INFORMATION: Primer

<400> SEQUENCE: 48
aacccggccc atttctacga agag                                     24

<210> SEQ ID NO 49
<211> LENGTH: 26
<212> TYPE: DNA
<213> ORGANISM: Artificial sequence
<220> FEATURE:
<223> OTHER INFORMATION: Primer

<400> SEQUENCE: 49
atgctgtgcc tacgggtaat taggga                                   26

<210> SEQ ID NO 50
<211> LENGTH: 24
<212> TYPE: DNA
<213> ORGANISM: Artificial sequence
<220> FEATURE:
<223> OTHER INFORMATION: Primer
```

```
<400> SEQUENCE: 50
gatttggccg gtacgactct cgtt                                              24

<210> SEQ ID NO 51
<211> LENGTH: 24
<212> TYPE: DNA
<213> ORGANISM: Artificial sequence
<220> FEATURE:
<223> OTHER INFORMATION: Primer

<400> SEQUENCE: 51
cgacctggat ctgcgatgtc gttg                                              24

<210> SEQ ID NO 52
<211> LENGTH: 24
<212> TYPE: DNA
<213> ORGANISM: Artificial sequence
<220> FEATURE:
<223> OTHER INFORMATION: Primer

<400> SEQUENCE: 52
cgttcagcga agacaggcag caac                                              24

<210> SEQ ID NO 53
<211> LENGTH: 40
<212> TYPE: DNA
<213> ORGANISM: Artificial sequence
<220> FEATURE:
<223> OTHER INFORMATION: Primer

<400> SEQUENCE: 53
cggtacccgg ggatcggaat tgctccaact ctcggctttc                             40

<210> SEQ ID NO 54
<211> LENGTH: 39
<212> TYPE: DNA
<213> ORGANISM: Artificial sequence
<220> FEATURE:
<223> OTHER INFORMATION: Primer

<400> SEQUENCE: 54
tagcaataag cccaaagggc aatgcacata gaaacacac                              39

<210> SEQ ID NO 55
<211> LENGTH: 40
<212> TYPE: DNA
<213> ORGANISM: Artificial sequence
<220> FEATURE:
<223> OTHER INFORMATION: Primer

<400> SEQUENCE: 55
tcttctgagg tgcgggcatg ggatttaagg gcatcattgg                             40

<210> SEQ ID NO 56
<211> LENGTH: 40
<212> TYPE: DNA
<213> ORGANISM: Artificial sequence
<220> FEATURE:
<223> OTHER INFORMATION: Primer

<400> SEQUENCE: 56
cgactctaga ggatcacttc ctggcctctc atcattcgca                             40

<210> SEQ ID NO 57
```

```
<211> LENGTH: 25
<212> TYPE: DNA
<213> ORGANISM: Artificial sequence
<220> FEATURE:
<223> OTHER INFORMATION: Primer

<400> SEQUENCE: 57
ggaattgctc caactctcgg ctttc                                      25

<210> SEQ ID NO 58
<211> LENGTH: 25
<212> TYPE: DNA
<213> ORGANISM: Artificial sequence
<220> FEATURE:
<223> OTHER INFORMATION: Primer

<400> SEQUENCE: 58
acttcctggc ctctcatcat tcgca                                      25

<210> SEQ ID NO 59
<211> LENGTH: 26
<212> TYPE: DNA
<213> ORGANISM: Artificial sequence
<220> FEATURE:
<223> OTHER INFORMATION: Primer

<400> SEQUENCE: 59
tccaggctgc ctatgacctt aacctg                                     26

<210> SEQ ID NO 60
<211> LENGTH: 26
<212> TYPE: DNA
<213> ORGANISM: Artificial sequence
<220> FEATURE:
<223> OTHER INFORMATION: Primer

<400> SEQUENCE: 60
ggctacggga gtagtgatac aaccga                                     26

<210> SEQ ID NO 61
<211> LENGTH: 26
<212> TYPE: DNA
<213> ORGANISM: Artificial sequence
<220> FEATURE:
<223> OTHER INFORMATION: Primer

<400> SEQUENCE: 61
ccaagtcgca attgacctac agcgca                                     26

<210> SEQ ID NO 62
<211> LENGTH: 26
<212> TYPE: DNA
<213> ORGANISM: Artificial sequence
<220> FEATURE:
<223> OTHER INFORMATION: Primer

<400> SEQUENCE: 62
atcccatccc tctttctggt accgct                                     26

<210> SEQ ID NO 63
<211> LENGTH: 26
<212> TYPE: DNA
<213> ORGANISM: Artificial sequence
<220> FEATURE:
<223> OTHER INFORMATION: Primer
```

```
<400> SEQUENCE: 63
caaagtgatc tccgaggctt tggatg                                                26

<210> SEQ ID NO 64
<211> LENGTH: 26
<212> TYPE: DNA
<213> ORGANISM: Artificial sequence
<220> FEATURE:
<223> OTHER INFORMATION: Primer

<400> SEQUENCE: 64
cagaatctct acgtccgaac cagtca                                                26

<210> SEQ ID NO 65
<211> LENGTH: 40
<212> TYPE: DNA
<213> ORGANISM: Artificial sequence
<220> FEATURE:
<223> OTHER INFORMATION: Primer

<400> SEQUENCE: 65
cggtacccgg ggatctccga tcttccttct catcaccctt                                 40

<210> SEQ ID NO 66
<211> LENGTH: 25
<212> TYPE: DNA
<213> ORGANISM: Artificial sequence
<220> FEATURE:
<223> OTHER INFORMATION: Primer

<400> SEQUENCE: 66
gcctggttat gttggatgtg tcaag                                                 25

<210> SEQ ID NO 67
<211> LENGTH: 40
<212> TYPE: DNA
<213> ORGANISM: Artificial sequence
<220> FEATURE:
<223> OTHER INFORMATION: Primer

<400> SEQUENCE: 67
ccaacataac caggcgatcc ctaaacatga ccagcttcag                                 40

<210> SEQ ID NO 68
<211> LENGTH: 40
<212> TYPE: DNA
<213> ORGANISM: Artificial sequence
<220> FEATURE:
<223> OTHER INFORMATION: Primer

<400> SEQUENCE: 68
catcgagcaa ctagaccata cgtcagatgc atcgccgtaa                                 40

<210> SEQ ID NO 69
<211> LENGTH: 24
<212> TYPE: DNA
<213> ORGANISM: Artificial sequence
<220> FEATURE:
<223> OTHER INFORMATION: Primer

<400> SEQUENCE: 69
tctagttgct cgatgtgatg cgaa                                                  24

<210> SEQ ID NO 70
```

```
<211> LENGTH: 26
<212> TYPE: DNA
<213> ORGANISM: Artificial sequence
<220> FEATURE:
<223> OTHER INFORMATION: Primer

<400> SEQUENCE: 70
gggagaggta aagattccag tggatg                                          26

<210> SEQ ID NO 71
<211> LENGTH: 39
<212> TYPE: DNA
<213> ORGANISM: Artificial sequence
<220> FEATURE:
<223> OTHER INFORMATION: Primer

<400> SEQUENCE: 71
atctttacct ctccctgctt tgtgcggagt ctctgtagg                            39

<210> SEQ ID NO 72
<211> LENGTH: 40
<212> TYPE: DNA
<213> ORGANISM: Artificial sequence
<220> FEATURE:
<223> OTHER INFORMATION: Primer

<400> SEQUENCE: 72
cgactctaga ggatcataca tctcgtgttg ggcaagacag                           40

<210> SEQ ID NO 73
<211> LENGTH: 25
<212> TYPE: DNA
<213> ORGANISM: Artificial sequence
<220> FEATURE:
<223> OTHER INFORMATION: Primer

<400> SEQUENCE: 73
tccgatcttc cttctcatca ccctt                                           25

<210> SEQ ID NO 74
<211> LENGTH: 25
<212> TYPE: DNA
<213> ORGANISM: Artificial sequence
<220> FEATURE:
<223> OTHER INFORMATION: Primer

<400> SEQUENCE: 74
atacatctcg tgttgggcaa gacag                                           25

<210> SEQ ID NO 75
<211> LENGTH: 26
<212> TYPE: DNA
<213> ORGANISM: Artificial sequence
<220> FEATURE:
<223> OTHER INFORMATION: Primer

<400> SEQUENCE: 75
ggggatacga atcttccctc tccagt                                          26

<210> SEQ ID NO 76
<211> LENGTH: 26
<212> TYPE: DNA
<213> ORGANISM: Artificial sequence
<220> FEATURE:
<223> OTHER INFORMATION: Primer
```

```
<400> SEQUENCE: 76
gtaatcgtgc acccagatca atgacc                                          26

<210> SEQ ID NO 77
<211> LENGTH: 26
<212> TYPE: DNA
<213> ORGANISM: Artificial sequence
<220> FEATURE:
<223> OTHER INFORMATION: Primer

<400> SEQUENCE: 77
gacaggaatc ggaaaagtcc gcatct                                          26

<210> SEQ ID NO 78
<211> LENGTH: 27
<212> TYPE: DNA
<213> ORGANISM: Artificial sequence
<220> FEATURE:
<223> OTHER INFORMATION: Primer

<400> SEQUENCE: 78
tcgaactact ggaagactgc accttct                                         27

<210> SEQ ID NO 79
<211> LENGTH: 22
<212> TYPE: DNA
<213> ORGANISM: Artificial sequence
<220> FEATURE:
<223> OTHER INFORMATION: Primer

<400> SEQUENCE: 79
tgcgtgagaa tcgtaagcgc ag                                              22

<210> SEQ ID NO 80
<211> LENGTH: 28
<212> TYPE: DNA
<213> ORGANISM: Artificial sequence
<220> FEATURE:
<223> OTHER INFORMATION: Primer

<400> SEQUENCE: 80
ttgggcttat tgctatgtcc ctgaaagg                                        28

<210> SEQ ID NO 81
<211> LENGTH: 39
<212> TYPE: DNA
<213> ORGANISM: Artificial sequence
<220> FEATURE:
<223> OTHER INFORMATION: Primer

<400> SEQUENCE: 81
tacgattctc acgcacttcc aacaccttaa gcgccaaga                            39

<210> SEQ ID NO 82
<211> LENGTH: 40
<212> TYPE: DNA
<213> ORGANISM: Artificial sequence
<220> FEATURE:
<223> OTHER INFORMATION: Primer

<400> SEQUENCE: 82
tagcaataag cccaacaccg taaagcctaa tgagggtgaa                           40

<210> SEQ ID NO 83
```

```
<211> LENGTH: 25
<212> TYPE: DNA
<213> ORGANISM: Artificial sequence
<220> FEATURE:
<223> OTHER INFORMATION: Primer

<400> SEQUENCE: 83
gtcatcccca ttatccgagc catca                                          25

<210> SEQ ID NO 84
<211> LENGTH: 39
<212> TYPE: DNA
<213> ORGANISM: Artificial sequence
<220> FEATURE:
<223> OTHER INFORMATION: Primer

<400> SEQUENCE: 84
cggtacccgg ggatcatgga actgacgtcc ttgaggcgt                           39

<210> SEQ ID NO 85
<211> LENGTH: 27
<212> TYPE: DNA
<213> ORGANISM: Artificial sequence
<220> FEATURE:
<223> OTHER INFORMATION: Primer

<400> SEQUENCE: 85
acgttgaatt gcctttcagt caccoct                                        27

<210> SEQ ID NO 86
<211> LENGTH: 40
<212> TYPE: DNA
<213> ORGANISM: Artificial sequence
<220> FEATURE:
<223> OTHER INFORMATION: Primer

<400> SEQUENCE: 86
aaggcaattc aacgttgtcg ggtttccata aggacgagga                          40

<210> SEQ ID NO 87
<211> LENGTH: 39
<212> TYPE: DNA
<213> ORGANISM: Artificial sequence
<220> FEATURE:
<223> OTHER INFORMATION: Primer

<400> SEQUENCE: 87
tagcaataag cccaaatgat gcggtggcat tcaagccga                           39

<210> SEQ ID NO 88
<211> LENGTH: 39
<212> TYPE: DNA
<213> ORGANISM: Artificial sequence
<220> FEATURE:
<223> OTHER INFORMATION: Primer

<400> SEQUENCE: 88
tcttctgagg tgcggttccg caatggtatg ctcccgatc                           39

<210> SEQ ID NO 89
<211> LENGTH: 39
<212> TYPE: DNA
<213> ORGANISM: Artificial sequence
<220> FEATURE:
<223> OTHER INFORMATION: Primer
```

```
<400> SEQUENCE: 89
cgactctaga ggatcaccaa ggattcaccc accttgctc                              39

<210> SEQ ID NO 90
<211> LENGTH: 24
<212> TYPE: DNA
<213> ORGANISM: Artificial sequence
<220> FEATURE:
<223> OTHER INFORMATION: Primer

<400> SEQUENCE: 90
atggaactga cgtccttgag gcgt                                              24

<210> SEQ ID NO 91
<211> LENGTH: 24
<212> TYPE: DNA
<213> ORGANISM: Artificial sequence
<220> FEATURE:
<223> OTHER INFORMATION: Primer

<400> SEQUENCE: 91
accaaggatt cacccacctt gctc                                              24

<210> SEQ ID NO 92
<211> LENGTH: 24
<212> TYPE: DNA
<213> ORGANISM: Artificial sequence
<220> FEATURE:
<223> OTHER INFORMATION: Primer

<400> SEQUENCE: 92
actccatcac aaacaggtca ttcg                                              24

<210> SEQ ID NO 93
<211> LENGTH: 22
<212> TYPE: DNA
<213> ORGANISM: Artificial sequence
<220> FEATURE:
<223> OTHER INFORMATION: Primer

<400> SEQUENCE: 93
cagagacact ttctgcaccg ga                                                22

<210> SEQ ID NO 94
<211> LENGTH: 25
<212> TYPE: DNA
<213> ORGANISM: Artificial sequence
<220> FEATURE:
<223> OTHER INFORMATION: Primer

<400> SEQUENCE: 94
ggcttgattg atgcgacgag acagt                                             25

<210> SEQ ID NO 95
<211> LENGTH: 26
<212> TYPE: DNA
<213> ORGANISM: Artificial sequence
<220> FEATURE:
<223> OTHER INFORMATION: Primer

<400> SEQUENCE: 95
acgaactggg tgtatgaggg tggtga                                            26
```